US00RE40480E

(19) United States
(12) Reissued Patent
Horrobin et al.

(10) Patent Number: US RE40,480 E
(45) Date of Reissued Patent: Sep. 2, 2008

(54) 1,3-PROPANE DIOL ESTERS AND ETHERS AND METHODS FOR THEIR USE IN DRUG DELIVERY

(75) Inventors: David B. Horrobin, deceased, late of Guildford (GB); by Sherri Clarkson, legal representative, Douglas (GB); Mehar Manku, Hollywood (GB); Philip Knowles, Cumbria (GB); Peter Redden, Oakville (CA); Andrea Pitt, Barnard Castle (GB); Paul Bradley, Hathern (GB); Paul Wakefield, Cumbria (GB); Austin McMordie, Craigavon (GB)

(73) Assignee: Scarista Limited, Douglas, Isle of Man (GB)

(21) Appl. No.: 11/405,041

(22) PCT Filed: May 1, 1996

(86) PCT No.: PCT/GB96/01053

§ 371 (c)(1),
(2), (4) Date: Jan. 28, 1998

(87) PCT Pub. No.: WO96/34846

PCT Pub. Date: Nov. 7, 1996

Related U.S. Patent Documents

Reissue of:
(64) Patent No.: 6,555,700
Issued: Apr. 29, 2003
Appl. No.: 08/945,667
Filed: Jan. 28, 1998

U.S. Applications:
(62) Division of application No. 11/119,495, filed on Apr. 29, 2005.

(30) Foreign Application Priority Data

May 1, 1995 (GB) ..... 9508823
Aug. 21, 1995 (GB) ..... 9517107
Mar. 15, 1996 (GB) ..... 9605440

(51) Int. Cl.
*C07C 57/13* (2006.01)

(52) U.S. Cl. ..... 514/29; 554/227; 554/82; 514/420; 549/39; 548/496; 560/38; 560/128

(58) Field of Classification Search ..... 548/496; 549/39; 560/38, 128
See application file for complete search history.

(56) References Cited

U.S. PATENT DOCUMENTS 2,924,528 A * 2/1960 Barsky et al. ..... 426/601
2,993,063 A * 7/1961 Alsop et al. ..... 554/169
3,291,816 A * 12/1966 Goldblatt et al. ..... 554/33
4,268,426 A * 5/1981 Williams et al. ..... 528/74.5
4,668,664 A * 5/1987 Rougier et al. ..... 514/29
4,851,426 A * 7/1989 Ladkani et al. ..... 514/420
5,286,512 A * 2/1994 Klemann et al. ..... 426/611
5,321,145 A * 6/1994 Schafer ..... 554/82

FOREIGN PATENT DOCUMENTS

EP 0 018 342 B1 * 2/1983
EP 0 087 864 A2 * 9/1983
EP 0 139 480 A2 * 5/1985
EP 0 139 780 A2 * 5/1985
EP 0161114 * 11/1985
EP 0 173 478 A1 * 3/1986
EP 0 057 797 B1 * 6/1986
EP 0 184 058 A2 * 6/1986
EP 0 056 189 B1 * 8/1986
EP 0 222 155 A1 * 5/1987

(Continued)

OTHER PUBLICATIONS

Breusch et al., Chemische Berichte, vol. 88, pp. 1511–1519, 1955.*
Langen et al., Chemical Abstracts, vol. 92, No. 1, #461a, 1980.*
Lion Corp., Patent Abstracts of Japan, vol. 6, No. 143(C–117), 1982.*
Vajdi et al., Chemical Abstracts, vol. 95, No. 5, #41676e, 1981.*
Hounsom et al., Oxidative Stress and Disease (2000), 4(Antioxidants in Diabetes Management), 155–172.*
Watanabe et al, Chemical Abstracts, vol. 107, No. 3, #23659p, 1987.*
Bertelsen, O. et al., "Structural Elucidation of Alkyl–Branched Chain Aliphatic Alcohols and Fatty Acids by Mass Spectrometry of their Respective Alkyl Nicotinate and Picolinylcarboxylate Derivatives," *Chemical Abstracts*, 104:108841 (1986).*
Christie, W.W., et al., "Mass Spectra of the Picolinyl Ester Derivatives of Some Isomeric Dimethylene–Interrupted Octadecadiynoic Acids," *Chemical Abstracts*, 109:210389(1988).*
Christie, W.W., et al., "Mass Spectra of the Picolinyl Esters of Isomeric Mono–and Dienoic Fatty Acids," *Chemical Abstracts* 107:55235 (1987).*

(Continued)

*Primary Examiner*—Rebecca L Anderson
(74) *Attorney, Agent, or Firm*—Buchanan Ingersoll & Rooney PC

(57) ABSTRACT

The invention relates to compounds of formula:

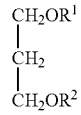

wherein $R^1$ is selected from the group consisting of fatty acid acyl groups of 12 to 30 carbon atoms and fatty alcohol groups of 12 to 30 carbon atoms, and wherein $R^2$ is selected from the group consisting of H, fatty acid acyl of 12 to 30 carbon atoms and fatty alcohol groups of 12 to 30 carbon atoms, the same as or different from $R^1$, and the residue of a nutrient, drug, or other bioactive compound, and to the use of these compounds to deliver drugs and other bioactive compounds.

7 Claims, No Drawings

FOREIGN PATENT DOCUMENTS

| | | | | |
|---|---|---|---|---|
| EP | 0 246 540 | A2 | * | 11/1987 |
| EP | 0 161 422 | B1 | * | 3/1989 |
| EP | 0319126 | | * | 6/1989 |
| EP | 0 321 128 | A1 | * | 6/1989 |
| EP | 0 393 920 | A2 | * | 10/1990 |
| EP | 0 405 873 | A1 | * | 1/1991 |
| EP | 0 405 874 | A1 | * | 1/1991 |
| EP | 0 574 312 | A1 | * | 12/1993 |
| EP | 0 611 569 | A2 | * | 8/1994 |
| EP | 0 675 103 | A2 | * | 10/1995 |
| FR | 1 782 | M | * | 4/1963 |
| GB | 0 888 162 | | * | 1/1962 |
| GB | 1 135 647 | | * | 12/1968 |
| GB | 1 293 277 | | * | 10/1972 |
| GB | 1 493 098 | | * | 11/1977 |
| GB | 1 529 762 | | * | 10/1978 |
| GB | 1 556 197 | | * | 11/1979 |
| GB | 2 161 477 | B | * | 9/1987 |
| JP | 57-067511 | | * | 4/1982 |
| JP | 61-129190 | | * | 6/1986 |
| JP | 2-129119 | | * | 5/1990 |
| JP | 4-99784 | | * | 3/1992 |
| JP | 05-051355 | | * | 3/1993 |
| WO | WO 91/09831 | | * | 7/1991 |
| WO | WO 94/26262 | | * | 11/1994 |
| WO | WO 95/04030 | | * | 2/1995 |
| WO | WO 96/33155 | | * | 10/1996 |

OTHER PUBLICATIONS

Deterding, L. et al., "Fast–Atom–Bombardment and Tandem Mass Spectrometry for Determining Structures of Fatty Acids and Their Picolyl Ester Derivatives," *Chemical Abstracts*, VI. 110:38801 (1989).*

Deterding, L., et al., "Tandem Mass Spectrometry for Identifying Fatty Acid Derivatives that Undergo Charge–Remote Fragmentations," *Chemical Abstracts* 110:56917 (1989).*

Harvey, D.J., Picolinyl Derivatives for the structural Determination of Fatty Acids by *Chemical Abstracts* 101:166564 (1984).*

Harvey, D.J., "Pyridine–Containing Derivatives for the Structural Elucidationof the Alkyl Chains of Lipids by Mass Spectrometry and a Comparison with the Spectra of Related Heterocyclic Derivatives," *Chemical Abstracts*, 114:206360 (1991).*

Jie, et al., "Mass Spectra of Picolinyl Ester Derivatives of Some Conjugated Diacetylenic Fatty Acids," *Chemical Abstracts*, 118:191384 (1993).*

Kimura, K. et al., Higher Unsaturated Fatty Alcohol Esters Having Antiucler Activity, *Chemical Abstracts*, vol. 87, 1997 Abstract No. 53462e.*

Koori, S., "Unsaturated Higher Akuogatuc Esters of Nicotinic Acid," *Chemical Abstracts*, vol. 77, Abstract No. 164488f (1972).*

Kumokawa, Y. et al. γ–Linolenic Acid Derivatives As Platelet Aggregation Inhibitors, *Chemical Abstracts*, vol. 105, 1986, Abstract No. 78532f.*

Spitzer, V. et al., "Curupira Tefeensis II: Occurrence of Acetylenic Fatty Acids," *Fat Sci. Technol.*, No. 5, (1991) pp. 169–174.*

Terumo Corp., "Trienoic Fatty Acid Pyridylmethyl Esters," *Chemical Abstracts*, vol. 101, 1984 Abstract No. 171104v.*

* cited by examiner

1,3-PROPANE DIOL ESTERS AND ETHERS AND METHODS FOR THEIR USE IN DRUG DELIVERY

Matter enclosed in heavy brackets [ ] appears in the original patent but forms no part of this reissue specification; matter printed in italics indicates the additions made by reissue.

*Notice: More than one reissue application has been filed for reissue on U.S. Pat. No. 6,555,700. U.S. application No. 11/405,041 (the present application) filed Apr. 14, 2006 is a divisional reissue of U.S. application No. 11/119,495 filed Apr. 29, 2005 which is a reissue of U.S. application No. 08/945,667 filed Jan. 28, 1998, now U.S. Pat. No. 6,555,700 which is a 371 of PCT/GB96/01053 filed May 1, 1996.*

This application is a 371 of PCT/GB96/01053, filed May 1, 1996.

FIELD

The specification relates to the presentation of bioactives, in which term we include a drug, essential nutrient or any other compound to be administered to the human or animal body in therapy or maintenance of health.

In particular, the specification relates to the presentation of such bioactives in a form in which they are lipophilic so that they can pass lipid barriers in the body readily, or to the presentation of two bioactives in the same molecule (where at least one of the bioactives is a fatty acid or fatty alcohol), or to the presentation of bioactives in a form which serves both aims and/or the aims of ready synthesis of such compounds without a chiral centre. From a drug regulatory viewpoint it is a great advantage to have two bioactives presented as a single molecule rather than as two separate entities. There may also be advantages in presenting known bioactives in novel ways. Those advantages include increased lipophilicity, the additives effects of two bioactives which are not normally presented together, and the sometimes synergistic effects of such bioactives.

The invention concerns the linking of bioactives through certain link molecules, considered in detail later herein, and the synthesis of a range of compounds some of which are entirely novel in themselves, while others are novel in the sense of their usefulness in therapy and/or the maintenance of health. Discussion is however, also given of compounds using other link molecules not currently claimed, and of directly linked bioactives, disclosed for example in EPA-0 393 920 concerning fatty acids and antivirals, and in co-pending EP-95301315.8 (published as EPA-0 675 103) concerning fatty acids and non-steroidal anti-inflammatory drugs.

Published Material

Concepts such as are discussed above have received no great attention in the published patent and general literature but there is material on certain specific natural diol derivatives and on nutritional and pharmaceutical uses of certain specific diol esters. A source paper in the general literature is Bergelson et al (Biochim. Biophys. Acta 1 16 (1966) 511–520) describing inter alia long chain diesters of 1,3-propane diol. Little is said of the acid moieties but dioleates are identified. In the patent literature edible fat mimetics are for example proposed by Nabisco in EPA-0 405 873 and EPA-0 405 874 and include linolenic acid esters (this term indicating the "alpha" isomer when not qualified otherwise) and arachidonic acid esters of, apparently, 1,4-butane diol.

Unilever's U.K. specification 2 161 477 (equivalent to EPA-0 161 114) concerns the growth and economic yield of plants, using inter alia 1,3-propane diol esters of linoleic acid and linolenic acid (again no doubt the alpha isomer). Anti-ulcer drugs of 2,3-butanediol esters are described in SS Pharmaceutical Co's EPA-0 056 189. Sundry pharmaceutical actions of propane-1,3-diol esters of short chain fatty acids are disclosed in Sanofi EPA-0 018 342. More distantly perhaps, Terumo K. K. in EPA-0 222 155 links 5-fluoro uracil to alpha linolenic acid, dihomo gamma linolenic acid, or eicosapentaenoic acid through a group —CH(R)—O— where R=methyl etc as, inter alia, anti-cancer agents.

Lipid Barriers

Many drugs act at the cell membrane surface by combining with cell surface receptors, or alternatively are taken into cells by specific transport systems. However, there are many drugs which, while they act within cells by modifying one of many different functions such as nucleic acid functions, the actions of intracellular enzymes, or the behaviour of systems like the lysosomes or the microtubules, are not able to penetrate cells effectively. There may be no receptors and transport systems with which they can link, or these systems may transport the drug into the cell at a less then optimum rate. Equally drugs may penetrate intracellular membranes such as mitochondrial and nuclear membranes at less than optimum rates.

There are other barriers to drug movements which are recognised as important. One of particular significance is the blood-brain barrier, which has many of the characteristics of the cell membrane. There are many drugs which have difficulty in reaching adequate concentrations in the brain because of this barrier. Another is the skin: until a few years ago drugs were applied to the skin only if their purpose was to act on the skin. However, it has been recognised that the skin can be an appropriate route for getting drugs with systemic actions into the body, and as a result more and more compounds are being administered by variations of patch technology.

All three types of barriers, the cell membrane and intracellular membranes, the blood-brain barrier and the skin have an important feature in common, they are substantially composed of lipids. What this means is that they are impermeable to primarily water-soluble drugs unless these drugs can be carried across the membrane by a receptor or transport system. In contrast, lipophilic substances are able to cross the barriers more readily without the need for any specific receptor or transport system.

Classes of Bioactives Requiring Passage Through Lipid Barriers

Drugs whose pharmacokinetic behaviour may be improved by increased lipophilicity, listed by route of entry, are as follows:

Cell entry: drugs particularly likely to benefit are those that act primarily intracellularly. These include:

a. All anti-inflammatory drugs, whether steroid or non-steroid b. All cytotoxic drugs used in the management of cancer;

c. All antiviral drugs;

d. All other drugs that have to enter cells in order to achieve optimum effects, in particular drugs which act on DNA or RNA, or on enzymes located intracellularly, or on second messenger systems, or on microtubules, mitochondria, lysosomes, or any other intracellular organelle.

e. Steroid hormones and other hormones that act intracellularly, such as oestrogens, progestins, androgenic hormones and dehydroepiandrosterone.

2. Blood-brain barrier: all drugs acting on the central nervous systems will have their transport improved by this technique. This includes all drugs used in psychiatry, all drugs used in cerebral infections with any organism or in cerebral cancer and all other drugs acting on nerve cells such as anti-epileptic drugs and others acting on neurological disorders such as multiple sclerosis, amyotrophic lateral sclerosis, Huntington's chorea and others.
3. Skin: as with the blood-brain barrier, all drugs that may be required to penetrate the skin to achieve a systemic effect will benefit from their conversion to a fatty acid derivatives.

For example, the approach discussed is applicable to amino acids. Of particular interest are those which seem to play roles in the regulation of cell function as well as acting as components of proteins. Examples include tryptophan (a precursor of 5-hydroxytryptamine [5-HT], a key regular of nerve and muscle function), phenylalanine (a precursor of catecholamines) and arginine (a regulator of the synthesis of nitric oxide which also plays important roles in controlling cellular activities).

Properties Conferred Generally

Generally the compounds proposed herein have many advantages in addition to their lipophilicity. Two moieties of a given fatty acid or even a single moiety may be delivered, in a form which is readily incorporated into the body as an oral, parenteral or topical formation; which is very well tolerated with none of the side effects associated, for example, with free fatty acids; which is not too stable to be properly utilised; which need have no chiral centre; and which is much more readily synthesised than the corresponding triglyceride with three moieties of the same fatty acid attached. Whereas triglycerides are well tolerated and well utilised, they are less desirable than the proposed compounds because they are more difficult to synthesise and may have a chiral centre with multiple potential isomers. Moreover with triglycerides the fatty acids may relatively easily migrate from one position to another creating new molecules not present in the original preparation. This obviously causes problems, particularly in the context of drug regulation where such instability may be unacceptable.

When two different fatty acids are to be delivered, the advantages are as before plus the ability to administer simultaneously two materials with different biological actions in a single molecule. This avoids the regulatory problems which ensue when two materials are administered as separate compounds, as well as the issues which arise where there is the possibility of chiral centres. When two drugs are delivered as separate molecules, regulatory authorities normally require each drug to be studied alone as well as in combination. If the two are combined in a single molecule, only the single molecule needs to be studied, greatly reducing the cost of development.

Where actives other than fatty acids are present there are similar advantages. The compounds allow drugs or other compounds to be administered in the form of relatively-lipophilic compounds which are non-chiral (unless the drugs or other compounds are themselves chiral), which release the active moieties relatively easily, and which are well tolerated on oral, topical or parenteral administration. Their lipophilicity enables them to be absorbed partially through the lymphatic system, so by-passing the liver; to cause less gastrointestinal irritation than with many compounds; and to facilitate transport of drugs and other agents across lipophilic barriers such as the skin, the cell membrane and the blood-brain barrier.

There is evidence that interesting specific properties in addition to ready passage of lipid barriers can be conferred on many drugs by making them more lipophilic. These properties include prolonged duration of action, reduction of side effects especially gastrointestinal, bypassing of first-pass liver metabolism and, potentially, site specific delivery of different materials.

Fatty Acid Derivatives; Effects of the Fatty Acids

The transport of actives across lipid membranes may be improved by linking them directly or via intermediate links to, in particular, gamma-linolenic acid (GLA) or dihomo-gamma-linolenic acid (DGLA), two fatty acids which in themselves have a range of desirable effects. These links also enable bioactive substances to be co-delivered in the same molecule with fatty acids which in themselves have desirable actions, irrespective of any transport advantages. Other fatty acids, such as any of the essential fatty acids (EFAs) and in particular the twelve natural acids of the n-6 and n-3 series EFAs (FIG. 1), can be used. Of these twelve, arachidonic acid, adrenic acid, stearidonic acid, eicosapentaenoic acid and docosahexaenoic acid are of particular interest because they in themselves have particularly desirable effects. Furthermore, any fatty acid, suitably $C_{12}$–$C_{30}$ or $C_{16}$–$C_{30}$ and desirably with two or more cis or trans carbon-carbon double bonds may also be of use. Use may be in the form of the fatty acid or the corresponding fatty alcohol. Conjugated linoleic and columbinic acids are examples of fatty acids which in themselves have valuable properties and are likely to be of particular use: References to fatty acids are accordingly to be read herein as to both forms, except where the chemistry of one or the other specifically is under discussion. The desirable properties of GLA and DGLA however, make them especially valuable for the purpose.

The essential fatty acids, which in nature are of the all—cis configuration, are systematically named as derivatives of the corresponding octadecanoic, eicosanoic or docosanoic acids, e.g. z,z-octadeca-9,12-dienoic acid or z,z,z,z,z,z-docosa-4,7,10,13,16,19-hexaenoic acid, but numerical designations based on the number of carbon atoms, the number of centres of unsaturation and the number of carbon atoms from the end of the chain to where the unsaturation begins, such as, correspondingly, 18:2n-6 or 22:6n-3 are convenient. Initials, e.g., EPA and shortened forms of the name e.g. eicosapentaenoic acid are used as trivial names in some of the cases.

FIG. 1

| n-6 EFA's | | n-3 EFA's |
|---|---|---|
| 18:2n-6 | | 18:3n-3 |
| (Linoleic acid, LA) | | (α-Linolenic acid, ALA) |
| ↓ | δ-6-desaturase | ↓ |
| 18:3n-6 | | 18:4n-3 |
| (γ-Linolenic acid, GLA) | | (Stearidonic acid, SA) |
| ↓ | elongation | ↓ |
| 20:3n-6 | | 20:4n-3 |
| (Dihomo-γ-linolenic acid, DGLA) | | |
| ↓ | δ-5-desaturase | ↓ |
| 20:4n-6 | | 20:5n-6 |
| (Arachidonic acid, AA) | | (Eicosapentaenoic acid, EPA) |

-continued

| FIG. 1 | | |
|---|---|---|
| ↓ | elongation | ↓ |
| 22:4n-6 (Adrenic acid) | | 22:5n-3 |
| ↓ | δ-4-desaturase | ↓ |
| 22:5n-6 | | 22:6n-3 (Docosahexaenoic acid, DHA) |

GLA and DGLA

In their own right GLA and DGLA have been shown to have anti-inflammatory effects, to lower blood pressure, to inhibit platelet aggregation, to lower cholesterol levels, to inhibit cancer cell growth, to reduce dyskinetic movements, to relieve breast pain, to improve calcium absorption and enhance its deposition in bone, to reduce the adverse effects of ionising radiation, to treat various psychiatric disorders, to cause vasodilation, to improve renal function, to treat the complications of diabetes, to dilate blood vessels and so on. Activities linked to GLA and DGLA will therefore not only become more lipophilic, enhancing penetration across all membranes, the skin and the blood brain barrier, but are also likely to exhibit new and additional therapeutic effects. The fatty acid compounds may thus be mutual bipartate prodrugs (if linked directly) or mutual tripartate prodrugs (if connected via a link).

Other fatty acids likely to be of especial value in this context are arachidonic acid and docosahexaenoic acid which are major constituents of all cell membranes; adrenic acid; and stearidonic acid and eicosapentaenoic acid which have ranges of desirable properties similar to those of GLA and DGLA. Fatty acids not included in the fatty acids of FIG. 1 which are of particular interest are conjugated linoleic acid (cLA) and columbinic acid (CA). cLA has a range of interesting effects in treating and preventing cancer, in promoting growth particularly of protein-containing tissues, in preventing and treating cardiovascular disease and as an antioxidant. CA has many of the properties of essential fatty acids.

Classes of Actives Having Mutual Efficacy with Bioactive Fatty Acids

Kinds of actives to be incorporated in compounds as set out herein may be broadly stated:

a) Drugs including antibiotics, antiprotozoals, antipsychotics, antidepressants and NSAIDS and compounds used in the treatment of cardiovascular, respiratory, dermatological, psychiatric, neurological, renal, muscular, gastrointestinal, reproductive and other diseases and in cancer.

b) Hormones c) Amino acids d) Vitamins particularly of the B group, and other essential nutrients.

e) Cytokines and peptides f) Neurotransmitters and neurotransmitter precursors.

g) Phospholipid head groups such as inositol, choline, serine and ethanolamine, which may be linked directly or via the phosphate moiety.

h) Aromatic fatty acids such as phenylacetic acid, phenyl butyric acid and cinnamic acid which are of particular value in cancer treatment.

Efficacy

The combination of the therapeutic effect of a drug with the therapeutic effect of a fatty acid may be considered through examples:

a) Psychotropic drugs may be linked to fatty acids such as GLA, DGLA, arachidonic acid, eicosapentaenoic acid or docosahexaenoic acid which have important roles in brain function, so providing a dual therapeutic effect.

b) Drugs used for the treatment of cardiovascular disease may be attached to a fatty acid which also has value in such treatment, such as eicosapentaenoic acid which lowers triglyceride levels and inhibits platelet aggregation, or GLA or DGLA which lower cholesterol levels and have vasodilator action, or arachidonic acid which is a potent cholesterol lower agenting, or DHA which has anti-arrhythmic properties.

c) Drugs used in the treatment of any form of inflammation may be linked to a fatty acid such as gammalinolenic acid, dihomo-gammalinolenic acid or eicosapentaenoic acid or docosahexaenoic acid which also has anti-inflammatory action.

d) Drugs used in the management of osteoporosis may be linked to GLA or DGLA which enhance the incorporation of calcium into bone, or to EPA or DHA which reduces urinary calcium excretion.

e) Drugs used in skin disease may be linked to GLA or DGLA which have anti-inflammatory effects on the skin.

f) Drugs used in cancer may be linked to GLA, DGLA, arachidonic acid, EPA or DHA which have anticancer effects in their own right and which may reverse resistance to anticancer drugs.

Concepts Applied to Essential Fatty Acids as Bioactives

The essential fatty acids (EFAs) as already referred to, and well known, consist of a series of twelve compounds. Although linoleic acid, the parent compound of the n-6 series, and alpha-linolenic acid, the parent compound of the n-3 series, are the main dietary EFAs, these substances as such have relatively minor roles in the body. In order to be fully useful to the body, the parent compounds must be metabolised to longer chain and more highly unsaturated compounds. In quantitative terms, as judged by their levels in cell membranes and in other lipid reactions dihomogammalinolenic acid (DGLA) and arachidonic acid (AA) are the main EFA metabolites of the n-6 series while eicosapentaenoic acid (EPA) and docosahexaenoic acid (DHA) are the main metabolites of the n-3 series. DGLA, AA, EPA and DHA are important constituents of most of the lipids in the body. As well as being important in themselves they can also give rise to a wide range of oxygenated derivatives, the eicosanoids, including the prostaglandins, leukotrienes and other compounds. The fatty acids likely to be of particular value in therapy are DGLA, AA, EPA and DHA, together with GLA, the precursor of DGLA, stearidonic acid (SA), the precursor of EPA and DPA (22:5n-3), the precursor of DHA, and adrenic acid.

Further there are fatty acids such as oleic acid, parinaric acid and columbinic acid that are not EFAs but may have significant effects in the body. One of the most interesting of these is conjugated linoleic acid which as noted earlier has a range of desirable effects.

It used to be thought that, both in nutrition and in therapy of disease, it was sufficient to supply linoleic and alpha-linolenic acids and the body's own metabolism would do the rest. It is now widely accepted that this is not true. Different diseases may have different abnormal patterns of EFAs and because of problems in metabolism these cannot simply be corrected by giving linoleic or alpha-linolenic acid. It is therefore appropriate in many situations to provide increased amounts of one of the other EFAs or to give two or more of the EFAs simultaneously. While the EFAs can be supplied in various forms and in various mixtures, it is convenient in both nutrition and in medical treatment to be able to supply the fatty acids as particular molecules. Equally in various situations it may be desirable to give the EFA or other fatty acid in association with an amino acid, vitamin, drug or other molecule which in itself has desirable properties.

To date, proposals for administration of two fatty acids simultaneously have been in terms of particular triglycerides, following the natural occurrence of essential fatty acids in triglycerides form. However, triglycerides, unless symmetrical about the 2-carbon, are chiral and that fact, coupled with acyl migration between the alpha and beta positions makes the synthesis of specific triglycerides a difficult task. Such migration may take place after synthesis creating particular problems in a drug regulatory context. The lack of specificity when two fatty acids are present in the same triglyceride molecule creates many problems in synthesis, pharmacology, formulation and stability. Moreover triglycerides can be slow and difficult to synthesise. When treated under similar conditions propane diol derivatives can be made much more rapidly.

For purposes of convenient administration of different fatty acids simultaneously or indeed of a single fatty acid in high amounts in well tolerated form, use is thus desirably made of esters of diols.

Chemical Nature of Bioactives which may be Derivatised According to the Present Disclosure The present specification covers fatty acid (or fatty alcohol) derivatives of bioactives with an available carboxyl, alcohol or amino group such that a single, well defined chemical entity is formed. The coupling may be direct yielding bipartate compounds or spaced with an appropriate link group, yielding tripartate compounds, in terms of the number of moieties into which the compounds split.

Classes of Bioactives by Chemistry

Among the classes of compounds are those below, where n is conveniently 1 to 3. The substances claimed herein include diesters of class (a) (ii); n=3. Also claimed are phosphate esters of class (b) (iv); n=3. Substances where n is a greater or lesser number, or where the links are not ester links, may be of value for similar reasons and are disclosed but largely not claimed currently.

(a) Bioactives with a free carboxyl group—these may be derivatised as follows:

(i) ester coupling with unsaturated fatty alcohol (UFA)

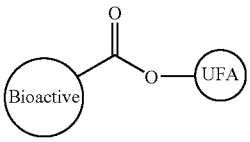

-continued (ii) ester coupling with ω-hydroxyalkyl ester of unsaturated fatty acid

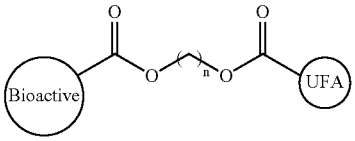

(iii) ester coupling with ω-hydroxyalkylcarboxy ester of unsaturated fatty alcohol.

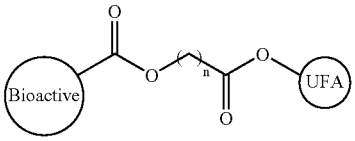

(b) bioactives with a free hydroxyl group—these may be derivatised as follows:

(i) ester coupling with unsaturated fatty acid

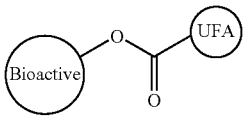

(ii) ester coupling with ω-carboxyalkylcarboxy ester of unsaturated fatty alcohol

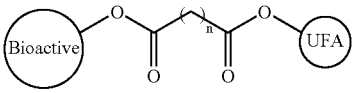

(iii) ester coupling with ω-carboxyalkyl ester of unsaturated fatty acid

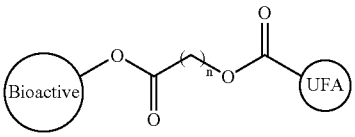

(iv) phosphate ester coupling with ω-hydroxyalkyl ester of unsaturated fatty acid

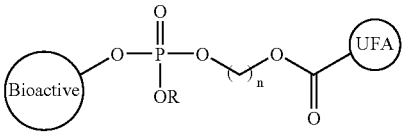

R═H, $CH_3$, or a cationic counterion (c) bioactives with a free amino group—these may be derivatives as follows:

(i) amide coupling with essential fatty acid

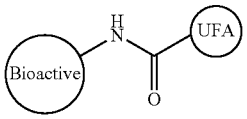

(ii) amide coupling with ω-carboxyalkylcarboxy ester of essential fatty alcohol

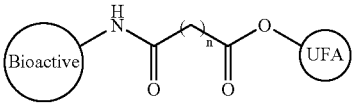

(iii) amide coupling with ω-carboxyalkyl ester of essential fatty acid

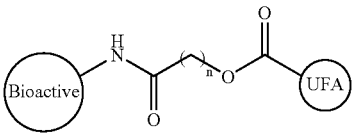

In all of the above categories where n is suitably 1 to 3, the carbon chain of the unsaturated fatty acid or alcohol is represented by:

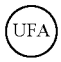

In all of these categories "unsaturated fatty acid" (and the derived "unsaturated fatty alcohol") represents a member of a group comprising oleic acid (and oleoyl alcohol) and any fatty acid (or corresponding fatty alcohol) with two or more cis or trans double bonds. However, the fatty acids likely to be of most value in this context are the essential fatty acids shown in FIG. 1 and in particular GLA, DGLA, AA, SA, EPA and DHA. For particular purposes conjugated linoleic acid and columbinic acid may be of great interest.

General Discussion of Synthesis

The individual fatty acids may be purified from natural animal, vegetable or microbial sources or may be chemically synthesized by methods known to those skilled in the art or developed hereafter.

The individual fatty alcohols may be prepared by chemical reduction of the fatty acids outlined above by methods known to those skilled in the art or developed hereafter.

Derivatisation of bioactives in classes (a), (b) and (c) [subclasses (ii) and (iii)] requires the formation of one or more ester bonds. Such chemistry may be achieved by any reasonable method of ester synthesis and especially:

(a) by reaction of alcohol with acid chloride, acid anhydride or suitably activated ester with or without the presence of an organic tertiary base, e.g. pyridine, in a suitable inert solvent, e.g. dichloromethane, at a temperature between 0° and 120° C.

(b) by reaction of alcohol with acid or acid, short or medium chain alkyl ester, in the presence of a suitable acid catalyst, e.g. 4-toluene sulfonic acid, with or without a suitable inert solvent, e.g. toluene, at a temperature between 500 and 180° C. such that the water formed in the reaction is removed, e.g. under vacuum.

(c) by reaction of alcohol with acid in the presence of a condensing agent, e.g. 1,3-dicyclohexylcarbodiimide, with or without the presence of a suitable organic tertiary base, e.g. 4-(N,N-dimethylaminopyridine), in an inert solvent, e.g. dichloromethane, at a temperature between 0° and 50° C.

(d) by reaction of alcohol with acid or acid, short or medium chain alkyl ester, or acid, activated ester, e.g. vinyl, in the presence of a hydrolase enzyme, e.g. hog liver esterase, with or without a suitable solvent, e.g. hexane, at temperatures between 20° and 80° C. under conditions such that the water or alcohol or aldehyde byproduct is removed, e.g. under vacuum.

(e) by reaction of acid with suitable alcohol derivative, e.g. iodide, with or without the presence of a suitable base, e.g. potassium carbonate, in a suitable inert solvent, e.g. dimethylformamide, at a temperature between 0° and 180° C.

(f) by reaction of alcohol with acid, short or medium chain alkyl ester, in the presence of a catalytic amount of an alkoxide of type M+OY— where M is an alkali or alkaline earth metal, e.g. sodium, and Y is an alkyl group containing 14 carbon atoms which may be branched, unbranched, saturated or unsaturated, with or without the presence of a suitable solvent, e.g. toluene, at temperatures between 50° and 180° C. such that the lower alcohol, HOY, is removed from the reaction mixture, e.g. under vacuum.

Derivatisation of bioactives in class (c) require the formation of an amide bond. Such chemistry may be achieved by any reasonable method of amide synthesis and especially:

(g) by reaction of amine with acid chloride, acid anhydride or suitably activated ester with or without the presence of an organic tertiary base, e.g. pyridine, in a suitable inert solvent, e.g dichloromethane, at a temperature between 0° and 120° C.

(h) by reaction of amine with acid in the presence of a condensing agent, e.g. 1,3-dicyclohexylcarbodiimide, with or without the presence of a suitable organic tertiary base, e.g. 4-(N,N-dimethylaminopyridine), in an inert solvent, e.g. dichloromethane, at a temperature between 0° and 50° C.

(i) by reaction of amine with acid or acid, short or medium chain alkyl ester, or acid, activated ester, e.g. vinyl, in the presence of a hydrolase enzyme, e.g. hog liver esterase, with or without a suitable solvent, e.g. hexane, at temperatures between 20° and 80° C. under conditions such that the water or alcohol or aldehyde byproduct is removed, e.g. under vacuum.

Derivatisation of bioactives in class (b) (iv) requires the formation of phosphate ester bonds. Such chemistry may be achieved by any reasonable method of phosphate ester synthesis and especially:

(j) by reaction of alcohol (e.g. UFA, 3-hydroxypropyl ester) with a suitably activated phosphate derivative (e.g. $POCl_3$) with a tertiary base (e.g. $Et_3N$) in a suitable solvent (e.g. THF) at a temperature less than 10° C. to yield crude phosphorodichloridate. This is followed by reaction of alcohol (e.g. α-tocopherol) with the crude phosphorodichloridate with a tertiary base (e.g. $Et_3N$) in a suitable solvent (e.g. THF) at around ambient temperature to yield crude phosphorochloridate. This may be hydrolysed (e.g. by addition of water and $Et_3N$) to yield phosphodiester. Alternatively, addition of methanol yields a phosphotriester which may be demethylated using a suitable nucleophile (e.g. lithium bromide) in a suitable solvent (e.g. methyl ethyl ketone) to yield the phosphodiester.

(k) by reaction of phosphomonoester (e.g. phosphate of UFA, 3-hydroxypropyl ester) with alcohol (e.g. choline) in the presence of a condensing agent (e.g. 1,3-dicyclohexylcarbodiimide) in a suitable solvent at a suitable temperature.

(l) transphosphatidylation reaction of 2-deoxy-2-lysophosphatidylcholine with primary or secondary alcohol catalysed by phospholipase D.

In general the chemistry of course depends on the nature of the compounds to be linked and on whether links are direct or indirect. Fatty acid pairs may for example be linked directly as fatty acid-fatty alcohol esters or as anhydrides, and if diol linkers are used ether links to fatty alcohols are an alternative to the more generally convenient ester links to fatty acids as such; in all cases linking may again be by chemistry known in itself.

Examples of Pairs of Actives which may be Linked either Directly or via a Link, Particularly a 1,3-Propane Diol Link Examples of pairs of actives follow, the resulting compounds listed being, to our knowledge, largely novel. So far as that is so, they represent part of the invention as new chemical entities, as well as being novel in use in treatment or prevention of disease, whether or not currently claimed.

Fatty Acids

GLA-OA (OA=Oleic Acid), GLA-GLA, EPA-EPA, GLA-EPA, GLA-DHA, AA-DHA, AA-EPA, GLA-AA, GLA-SA, SA-DHA, AA-SA, DGLA-DGLA, DGLA-GLA, DGLA-SA, DGLA-AA, DGLA-EPA, DGLA-DHA, AA-AA, EPA-SA, EPA-DHA, DHA-DHA, cLA-cLA, cLA-GLA, cLA-DGLA, cLA-AA, cLA-SA, cLA-EPA, cLA-DHA, CA-CA, CA-GLA, CA-DGLA, CA-AA, CA-SA, CA-EPA, CA-DHA.

Vitamins

GLA-niacin, GLA-retinoic acid, GLA-retinol, GLA-pyridoxal, Di-GLA-pyridoxine, di-EPA-pyridoxal and in general any of e.g. GLA, DGLA, AA, SA, EPA or DHA with any vitamin including ascorbic acid, Vitamin D and its derivatives and analogues, Vitamin E and its derivatives and analogues, Vitamin K and its derivatives and analogues, Vitamin $B_1$ (thiamin), Vitamin $B_2$ (riboflavin), folic acid and related pterins, Vitamin $B_{12}$, biotin and pantothenic acid.

Amino Acids

GLA-tryptophan, GLA-proline, GLA-arginine, GLA- or DHA-phenylalanine, GLA-GABA, GLA-aminolevulinic acid and in general any of e.g. GLA, DGLA, AA, SA, EPA or DHA with any natural amino acid or related compound such as taurine and carnitine.

Aromatic Acids

GLA-phenylbutyric acid, GLA-phenylacetic acid, GLA-trans-cinnamic acid and in general any of e.g. GLA, DGLA, AA, SA, EPA or DHA with any aryl alkanoic or aryl alkenoic acid.

Steroids

GLA-hydrocortisone, GLA-oestradiol, GLA- and DHA-dehydroepiandrosterone and in general any of e.g. GLA, DGLA, AA, SA, EPA or DHA with any natural or synthetic steroid, such as any oestrogen, any progestin, any adrenal steroid and any anti-inflammatory steroid, particularly betamethasone, prednisone, prednisolone, triamcinolone, budesonide, clobetasol, beclomethasone and other related steroids.

Anti-oxidants

GLA-lipoic acid, DHA-lipoic acid, GLA-tocopherol, di-GLA-3,3'-thiodipropionic acid and in general any of e.g. GLA, DGLA, AA, SA, EPA or DHA with any natural or synthetic anti-oxidant with which they can be chemically linked. These include phenolic anti-oxidants (e.g. eugenol, carnosic acid, caffeic acid, BHT, gallic acid, tocopherols, tocotrienols and flavonoid anti-oxidants (e.g. myricetin, fisetin)), polyenes (e.g. retinoic acid), unsaturated sterols (e.g. $\Delta^5$-avenosterol), organosulfur compunds (e.g. allicin), terpenes (e.g. geraniol, abietic acid) and amino acid anti-oxidants (e.g. cysteine, carnosine).

Drugs

GLA and indomethacin, ibuprofen, fluoxetine, ampicillin, penicillin V, sulindac, salicylic acid, metronidazole, fluphenazine, dapsone, tranylcypromine, acetyl carnitine, haloperidol, mepacrine, chloroquine, penicillin, tetracycyline, pravastatin, bisphosphonates such as efidronic acid, pamidronic acid and clordronic acid and their sodium salts, adenosylosuccinate and adenylosuccinate and related compounds and agents used as x-ray contrast media, and in general any of e.g. GLA, DGLA, AA, SA, EPA or DHA with any drug, particularly any drug used in the treatment of infections, inflammatory diseases, including various forms of arthritis, cancer, cardiovascular, respiratory, dermatological, psychiatric, neurological, muscular, renal, gastrointestinal, reproductive and other diseases.

Concepts Applied to NSAIDs; Effectiveness Shown

As a particular example of the concepts discussed, we have prepared derivatives of various non-steroidal anti-inflammatory drugs (NSAIDS) and in particular the GLA-ester of indomethacin. Indomethacin as a non-steroidal anti-inflammatory drug is believed to have a primarily intracellular mechanism of action by inhibiting the enzyme cyclo-oxygenase, which converts arachidonic acid to pro-inflammatory prostaglandin metabolites.

Indomethacin is known to penetrate cells very poorly and so has to be given in relatively large doses which can produce many side effects, thus indomethacin-GLA was compared with indomethacin itself for its ability to penetrate cells, using a normal fibroblast line, a breast cancer line and a malignant melanoma line.

The results are set out in EPA-0 675 103 and show that in all the cell lines the intracellular level of indomethacin after incubation with indomethacin is very low and is mainly detected only in trace amounts. In contrast, again in all cell lines, incubation with indomethacin-GLA resulted in very substantial amounts of both indomethacin-GLA and free indomethacin being found within the cells. These results show unequivocally that the GLA ester of indomethacin penetrates cells effectively and is then deterified intracellularly to provide free indomethacin, and that in view of the many similarities between the cell membrane barrier and the blood-brain and skin barriers, the indomethacin-GLA will also be effective in accelerating the penetration of indomethacin through these barriers. Such penetration, and breakdown to free the actives, is to be expected with all the compounds set out herein.

The Present Invention as Claimed

Aspects of the invention are set out in the claims herein, the main claim referring to compounds, when for use in therapy wherein a 1,3 propane diol residue forms a link between residues $R^1$ and $R^2$ where $R^1$ is an acyl or fatty alcohol group derived from a $C_{12-30}$ preferably $C_{16-30}$ fatty acid desirably with two or more cis or trans double bonds, and $R^2$ is hydrogen, or an acyl or fatty alcohol group as $R^1$ the same or different, or any other nutrient, drug or other bioactive residue.

The compounds will generally be acid-function bearing actives esterified directly to the diol residue but for example with a fatty alcohol or other hydroxy-function bearing active, a phosphate, succinate or other difunctional acid group may be interposed between the $R^1$ and/or $R^2$ group and the 1,3-propane diol residue, particularly when $R^2$ is a nutrient, drug or other bioactive with a hydroxy or amino function.

The invention is also discussed broadly below, concerning a wide range of actives releasable in the body.

While direct linkages of bioactives and fatty acids (classes (a)[i], (b)[i] and (c)[i] are discussed above, the present invention concerns primarily class (a)[ii], n=3 whereby bioactives, which may themselves be fatty acids, are linked to fatty acids as diesters of 1,3-propane diol and class (b)(iv), n=3 whereby bioactives, which may themselves be fatty alcohols or 3-hydroxypropyl esters of fatty acids, are linked via a phosphate linkage to a fatty acid monoester of 1,3-propane diol. This diol may also be regarded as 2-deoxyglycerol and the corresponding diesters as 2-deoxy-1,3-diglycerides. Compounds in class (b)(iv), n=3 are also based on 1,3-propane diol and may be regarded as 2-deoxy-2-tysophospholipids. The compounds listed herein are almost all new chemical entities or at least have never previously been used in treatment of human or animal disease.

As a compound the diol used as a link is, broadly, disclosed in the literature among many other diols but we have seen that its use in therapy in the form of an essential fatty acid diester or as a compound with an essential fatty acid at one position and a bioactive (not being an essential fatty acid) at the other, is both undisclosed and particularly significant. Indeed it offers a favourable way to give a single fatty acid as the monoester or diester if a completely defined compound is required, as there is no chiral centre such as is present in glycerol 1(3)-monoesters and in diglycerides (α,β and 1,3 where the fatty acid at position 1 is different from that at position 3), nor do positional isomers exist. Further, apart from administering individual acids, such mono and diesters may have value in pharmaceutical formulation as emulsifiers. The 1,3-propane diol structure is close to the glycerol of natural triglycerides and an effective and safe delivery system. Moreover it allows ready and unequivocal synthesis of defined compounds without the problems of acyl migration shown in triglycerides and without complications by optical isomers. We have for example shown that intravenous infusion and oral administration of a 1,3 propane diol GLA/EPA diester emulsion leads to rapid in vivo release of free GLA and EPA and to further metabolism of the GLA to AA and of the EPA to DHA. Similarly, GLA-GLA and EPA-EPA diesters, and niacin-GLA and indomethacin-GLA diesters have been shown to be absorbed following oral administration and to release their active moieties.

Furthermore, as far as we are aware, all of the 1,3-propane diol derived compounds set out on pages 17, 18 and 19 are novel compounds which have never before been described. The specific diols of fatty acids listed, and the diols where a fatty acid drawn from the list of GLA, DGLA, AA, SA, EPA, DHA, cLA and CA is present at one position and at the other position is a vitamin, amino acid, aromatic acid, steroid, anti-oxidant or other therapeutic drug, are new substances.

The fatty acid diesters have a wide variety of possible uses. They may be used as pharmaceuticals for the treatment or prevention of diseases in which abnormalities of fatty acids have been identified. They may be added to foods or added to or used as nutritional supplements for those who require the particular fatty acid for the treatment or prevention of diseases. They may also be used in foods or pharmaceuticals for veterinary use. They may further be used for skin care.

As advantages or in various particular aspects including those currently in the claims herein, the invention provides:

(i) A convenient and safe way of administering, for therapeutic or nutritional purposes, one or two unsaturated fatty acid moieties, or one unsaturated fatty acid and one bioactive that is not a fatty acid.

(ii) A derivative, of a bioactive required to cross lipid membranes in the body to exert its action whether in entry to a cell or in passing the skin, blood-brain or other barrier, through a 1,3-propane diol linkage to an essential fatty acid of the natural n-6 or n-3 series and especially GLA or DGLA, AA, SA, EPA or DHA or the related fatty acids cLA or CA.

(iii) A fatty acid derivative of a drug such that the drug and fatty acid are mutually efficacious.

(iv) A method of improving the transport of a drug across lipid membranes in the body, characterised by the administration of the drug in a form as above.

(v) A method of manufacture of a medicament for improved therapy involving transport of a drug across lipid membranes in the body, characterised by incorporating the drug in a medicament in a form as above.

(vi) A method of manufacture of a medicament for delivering one or two fatty acids from the list in (ii) above or for delivering one of those fatty acids in association with another active agent.

Examples of specific compounds have been given earlier herein; synthesis examples come later.

Efficacy and Uses Generally

Particular uses of particular groups of compounds are indicated elsewhere herein but the usefulness, generally, of the 1,3-propane diol diesters may be illustrated by the following:

1. Improved tolerability of fatty acids. Apart from the triglycerides, most forms in which fatty acids can be administered including free acids, salts, ethyl esters and other glycerides cause some degree of gastrointestinal intolerance as shown by nausea, vomiting and diarrhoea. The propane diol diesters in animal studies in rats and mice have been found to be extremely well tolerated. For example, the GLA-GLA and GLA-EPA diesters have been given to rats and mice at doses of up to 10 g/kg without any evidence or diarrhoea. This shows that the diesters are a very acceptable way of delivering biologically active fatty acids.
2. Reduced toxicity of drugs. The non-steroidal anti-inflammatory drugs such as aspirin and indomethacin are notorious for causing severe gastrointestinal toxicity with ulceration of the stomach and intestines and bleeding into the gastrointestinal tract. Doses of indomethacin known to cause gastrointestinal ulceration (5–30 mg/kg) were given to fasted rats either in the form of free indomnethacin or the same amount of indomethacin in a 1,3-propane diol diester with GLA in the other position. The animals were sacrificed after 24 hours and the whole gastrointestinal tract examined for ulceration. Whereas extensive ulceration was found in the animals treated with indomethacin alone, little or no ulceration was found in the animals treated with GLA-indomethacin.
3. Efficient delivery of a biologically active form of a fatty acid. GLA was administered in the form of either GLA-GLA or GLA-EPA and EPA was administered in the form of GLA-EPA or EPA-EPA. The diesters were given either orally by gavage or intravenously in the form of a 20% emulsion made using 2% of oat galactolipid as an emulsifier in doses from about 0.1 to 2.0 g/kg. Animals were killed after 1, 2, 4, 8 and 24 hours and plasma, red cells and liver collected. The presence of the unmetabolised diesters was identified by high pressure liquid chromatography. The presence of fatty acids derived from the diesters and of metabolites of those fatty acids was checked by lipid extraction of the liver, plasma or red cells, by separation of that lipid fraction into triglycerides, phospholipids, cholesterol esters and free fatty acids by thin layer chromatography, by methylation of the fatty acids derived from those separated fractions and by analysis of those fatty acids using gas chromatography using methods well described in standard texts. These experiments showed that after oral administration around 10% of the diester administered could be identified in the diester form. Most of the GLA or EPA was found in the free fatty acid or phospholipid and to a lesser extent in the cholesterol ester and triglyceride fractions. Moreover, particularly in the phospholipid fractions the metabolites of GLA, DGLA and arachidonic acid, and the metabolites of EPA, docosapentaenoic acid and DHA, could be found in increased amounts. These observations indicate that the fatty acids are readily released from the diester form and are then further metabolised into biologically active substances. Similar results were obtained from intravenous administration of the diester except that at one hour around 40% of the diester remained in the original form and the free fatty acids were released, metabolised and incorporated into other lipid fractions over the following 24 hours. It is possible that the unchanged diester forms may have biological activity themselves. Linoleic acid in a 1,3-diglyceride form has been found to have anticancer effects which were selective against cancer but not normal cells and which were not shared by other forms of linoleic acid (A. Matsuzaki et al, Cancer Res. 1989; 49: 5702–7). It is possible that this and perhaps other actions require the delivery of two molecules of the fatty acid spaced as in a 1,3-diglyceride. Similar spacing will be achieved by a 1,3-propane diol and there may therefore be a particular value in the intravenous administration of some of the propane diol derivatives which will ensure that the diol form circulates for some time before its complete metabolism.

The fatty acids have a large number of desirable biological and therapeutic activities which have been detailed in numerous publications by the inventors and by others. Four of the fatty acids, GLA, DGLA, SA and EPA share a rather broad spectrum of effects which include:

1. Cardiovascular actions including vasodilatation, lowering of blood pressure, inhibition of platelet aggregation, lowering of triglyceride and LDL-cholesterol levels, elevation of HDL-cholesterol levels and inhibition of smooth muscle proliferation.
2. Anti-inflammatory actions including reduction of formation of pro-inflammatory mediators such as cytokines, and of eicosanoids derived from arachidonic acid, reduction of neutrophil migration and the neutrophil respiratory burst, reduction of local inflammatory responses, inhibition of inflammation in various animal models such as uric acid induced inflammation and adjuvant arthritis, and treatment of various inflammatory disorders such as osteoarthritis and rheumatoid arthritis.
3. Immunomodulatory functions including the damping down of excessive immune and allergic responses in animal models such as experimental allergic encephalomyelitis and uveitis, bronchial and cutaneous hyperreactivity in sensitised animals, leading to the concept that they are of value in human diseases where excessive immune responses play a role.
4. Respiratory actions including bronchodilatation and inhibition of brochoconstrictor actions.
5. Improvements in calcium balance with increased calcium absorption, reduced calcium excretion, increased deposition of calcium in bones and reduced ectopic deposition of calcium in tissues such as arteries and kidneys.
6. Anticancer effects of three sorts, selective cytotoxic damage and induction of apoptosis in cancer cells but not in normal cells, inhibition of growth by reduction of action of growth factors and interference with second messenger systems required for growth, inhibition of metastasis by various actions including increased expression of E-cadherins and inhibition of proteolytic enzymes such as urokinases, lipoxygenase and matrix metalloproteinases, and inhibition of cancer-associated cachexia.
7. Actions on nerve cells including maintenance of normal nerve membrane structure and function and the normal pre- and post-synaptic actions of neurotransmitters.

These desirable actions mean that this group of fatty acids can be used in the treatment of may different disorders including cardiovascular disorders of many types, inflammatory disorders including rheumatoid arthritis, osteoarthritis, ulcerative colitis and Crohn's disease, respiratory disorders including asthma, psychiatric disorders including schizophrenia, alcoholism, attention deficit disorder, depression and Alzheimer's disease, neurological disorders including multiple sclerosis and Huntington's chorea, renal and urinary tract disorders including various types of renal inflammatory disease and urinary calcium stones, metabolic disorders including osteoporosis and ectopic calcification, and gastrointestinal ulcerative and inflammatory diseases. Although conjugated linoleic acid (cLA) has not been nearly as widely tested as, say GLA or EPA, it also seems to have a wide range of actions including effects valuable in the treatment of cancer, cardiovascular and metabolic diseases.

GLA, DGLA, AA and columbinic acid have desirable actions on the skin and are particularly valuable in the treatment of skin diseases such as atopic eczema, psoriasis, urticaria and allergic reactions.

AA is often regarded as a potentially harmful fatty acid. However, it is an essential constituent of all normal cell membranes and has been found to be present in low levels in various illnesses including atopic eczema, schizophrenia (Horrobin et al, Schizophrenia Res. 1994; 13: 194–207) and cardiovascular disorders (Horrobin, Prostaglandins Leukotr. EFAs 1995; 53: 385–96). AA is likely to be of particular value in these situations and also in other psychiatric disorders such as alcoholism and attention deficit disorder where levels are also often low.

DHA shares some of the above actions of the EFAs but is found in particularly important amounts in cell membranes and especially in the membranes of the heart, the retina and the brain. DHA also has potent anti-inflammatory and desirable cardiovascular effects. DHA is likely to be of particular value in cardiovascular disorders, in retinal and visual disorders including retinitis pigmentosa, senile macular degeneration and dyslexia, and in psychiatric and neurological disorders including schizophrenia, attention deficit disorder, depression, alcoholism, Alzheimer's disease and other forms of dementia and multiple sclerosis.

Infections have also recently been identified as likely to respond to fatty acids, especially to GLA and DGLA, EPA and DHA. Many bacteria are killed by these fatty acids, including strains which are highly resistant to antibiotics. Recent work from a number of laboratories has also shown that these highly unsaturated fatty acids are important in successful responses to diseases like malaria and to protozoal diseases.

It is thus apparent that various specific fatty acids are likely to be able to add to the efficacy of drugs and other bioactive substances of almost any class, in both the treatment and prevention of disease, in skin care and in nutrition, as well as having valuable therapeutic effects when given in the diol form as a single fatty acid or as two different fatty acids in the same molecule. Of particular value in therapy is that under most circumstances the fatty acids are remarkably non-toxic and can be administered safely in large doses without the risk of important side effects.

As a specific example of the therapeutic efficacy of the diesters, the 1,3 GLA-EPA propane diol diester was tested in the treatment of the ASPC-1 human pancreatic -cancer transplanted subcutaneously into nude mice which because they lack thymus function are able to accept foreign transplants without rejection. 15 mice were each injected subcutaneously with 15 million ASPC-1 cells suspended in Matrigel and DMEM buffer. In all animals a tumour developed whose size could be measured using callipers and whose volume could be estimated from the linear dimensions. Tumour size in each animal was measured twice weekly for five weeks.

The animals were divided into three groups. 5 animals were used as controls and received 10 g/kg corn oil per day only. 5 animals received 10 g/kg corn oil per day but in addition received two injections per week of a dose of 1.5 g/kg of the GLA-EPA diester. The diester was administered in the form of a 20% emulsion in which 2% of oat galactolipid was used as the emulsifier; the intravenous emulsion was very well tolerated and caused no haemolysis or thrombophlebitis or any other form of distress to the animals. The other 5 animals instead of the corn oil received 10 g/kg/day of the GLA-EPA diester. The treatments were continued for three weeks and then the tumours were allowed to grow for a further two weeks before the animals were sacrificed and the tumours excised and weighed. The mean tumour weights were: control group, 1240±290 mg; intravenous GLA-EPA group, 820±180 mg; oral GLA-EPA group, 490±160 mg. Tumour growth was thus substantially inhibited by both oral and intravenous administration of the GLA-EPA diester without causing any side effects or distress in the animals. This demonstrates that the GLA-EPA diester can be effectively used in the treatment of cancer as would be predicted by the effects of GLA and EPA given separately in being able selectively to kill human cancer cells in culture in the laboratory. Thus the diesters are biologically active ways of administering the various fatty acids. The diesters can therefore be reasonably expected to exert the many desirable effects of the fatty acids which have been noted in many publications in the literature (e.g. Horrobin D F, ed., Omega-6 Essential Fatty Acids: Pathophysiology and Roles in Clinical Medicine: Wiley-Liss, New York, 1990. Simopoulos A P et al, eds, Health Effects of Omega-3 Polyunsaturated Fatty Acids in Seafoods, Karger, Basel, 1991. Fats and Oils in Human Nutrition, World Health Organization, Rome, 1994. Unsaturated Fatty Acids: Nutritional and Physiological Significance. British Nutrition Foundation, Chapman and Hall, London, 1992).

Specific Uses of Particular 1,3-Propane Diol Compounds 1. 1,3-propane diol as derivatives containing: two fatty acids in which one fatty acid is GLA or DGLA and the other is GLA, DGLA, SA, EPA, DHA, cLA (conjugated linoleic acid) or CA (columbinic acid) for the treatment of:

(a) complications of diabetes, particularly neuropathy and retinopathy; and improvement of responses to insulin in diabetes and pre-diabetes;

(b) cancers;

(c) osteoarthritis;

(d) rheumatoid arthritis;

(e) other inflammatory and auto-immune diseases including Sjogren's syndrome, systemic lupus, ulcerative colitis, Crohn's disease and uveitis;

(f) respiratory diseases including asthma;

(g) neurological disorders including multiple sclerosis, Parkinson's disease and Huntington's chorea;

(h) renal and urinary tract disorders;

(i) cardiovascular disorders;

(j) degenerative diseases of the eye including retinitis pigmentosa and senile macular degeneration;

(k) psychiatric disorders including schizophrenia, Alzheimer's disease, attention deficit disorder, alcoholism and depression;

(l) prostatis hypertrophy and prostatitis;

(m) impotence and male infertility;

(n) mastalgia;

(o) male pattern baldness;

(p) osteoporosis;

(q) dermatological disorders, including atopic eczema, hand eczema, psoriasis, urticaria and allergic disorders;

(r) dyslexia and other learning disabilities;

(s) cancer cachexia.

2. 1,3-propane diol as derivatives containing two fatty acids in which one fatty acid is AA and the other is AA, GLA, DHA, DGLA or EPA for treatment of the disorders as at (1) above and especially (a), (g), (i), (k), (q) and (r).

3. 1,3-propane diol as derivatives containing two fatty acids in which one fatty acid is EPA and the other is EPA or DHA for the treatment of any of the disorders as at (1) above but especially (b), (c), (d), (e), (f), (g), (h), (i), (j), (k), (p), (r) and (s).

4. 1,3-propane diol as derivatives in which one position is occupied by a fatty acid drawn from GLA, DGLA, AA, SA, cLA, EPA or DHA and the other position is occupied by an agent, selected from the following list, whose chemical structure is such that it can be linked to the 1,3-propane diol by one of the linkages described herein:

(a) tryptophan for the treatment of any disease but particularly for psychiatric, neurological, behavioural, pain and other disorders and especially depression, sleep and migraine;

(b) phenylalanine for the treatment of any disease, but especially depression, multiple sclerosis and chronic fatigue syndrome;

(c) arginine for the treatment of any disease but particularly diseases in which the production of nitric oxide is defective;

(d) carnitine or carnitine derivatives for the treatment of any disease but especially muscle weakness, cardiac failure, chronic fatigue syndrome, Alzheimer's disease, and peripheral neuropathies;

(e) any other amino acid or related substance for the treatment of any disease or aminolevulinic acid or derivative thereof for the treatment of any disease but especially cancers;

(f) adenylosuccinate or related substances for the treatment of any disease but especially muscular dystrophy, cardiac failure, chronic fatigue and Alzheimer's disease and other dementias;

(g) aspirin, salicylic acid, indomethacin, ibuprofen, or any other non-steroidal anti-inflammatory drug for the treatment of any disease but especially of inflammatory disorders of pain, of Alzheimer's disease and other dementias and of any disease in which platelet aggregation should be inhibited;

(h) any antibiotic for the treatment of any appropriate infectious disease but especially tetracycline, clindamycin, minocycline, chlortetracycline and erythromycin for the treatment of acne;

(i) any anti malarial or anti-protozoal drug for the treatment of any disease, but especially chloroquine, mnepacrine, quinacrine and mefloquine for the treatment of malaria, protozoal disorders, inflammatory disorders and schizophrenia;

(j) any antifungal drug for the treatment of any disease but especially metronidazole and antifungal imidazoles and nitroimidazoles and amphotericin for the treatment of fungal infections of various types;

(k) any anti-inflammatory steroid for the treatment of any disease but especially hydrocortisone and betamethasone for the treatment of skin disorders and beclomethasone and budesonide for the treatment of asthma.

(l) any gonadal steroid for the treatment of any disease but especially oestrogens and progestogens for the treatment of ovarian deficiency and osteoporosis and androgens for the treatment of testicular deficiency;

(m) any adrenal steroid for the treatment of any disease, but especially dehydroepiandrosterone for the treatment of disorders associated with ageing;

(n) any retinoid for the treatment of any disease but especially tretinoin and isotretinoin for the treatment of dermatological disorders and for use in skin care;

(o) any anticancer agent for the treatment of cancer;

(p) any antipsychotic agent for the treatment of schizophrenia and other psychoses;

(q) any antidepressive agent for the treatment of any disease but especially for the treatment of depression;

(r) any anti-anxiety agent for the treatment of any disease, but especially for the treatment of anxiety and panic attacks;

(s) any immunosuppressive agent for the treatment of any disease but especially cyclosporine and tacrolimus for the control of immunity after organ transplantation and for the treatment of autoimmune and inflammatory disorders including psoriasis, eczema, asthma, rheumatoid arthritis and inflammatory bowel disease;

(t) any proton pump inhibitor or H2 antagonist for the treatment of any disease but especially diseases associated with excess gastric acid production or reduced defences against gastric acidity;

(u) any diuretic for any disease, but especially for diseases associated with fluid retention and hypertension;

(v) any calcium antagonist used for any disease but especially for cardiovascular diseases;

(w) any angiotensin converting enzyme inhibitor or angiotensin antagonist used for any disease but especially for cardiovascular diseases;

(x) any beta-blocker used for any disease but especially for cardiovascular disorders;

(y) any antiepileptic drug used for any disease, but especially phenytoin, carbamazepine, valproate, ethosuximide, vigabatrin or lamotrigine for the treatment of epilepsy;

(z) any hypolipidaemic agent for the treatment of any disease but especially fibrates and statins used for cholesterol lowering and cholesterol modification;

(aa) any oral hypoglycaemic or insulin-sensitising agents used in the management of diabetes;

(bb) any bisphosphonates used in the management of osteoporosis, Paget's disease or cancer;

(cc) any contrast agents used in radiology including diatrizoate compounds, iodipamide, ioglycamates, iopanoates, iophendylate, iothalamate, ioxaglate, metrizamide and related compounds;

(dd) any peptide or protein for use in the treatment of diseases for which the peptide or protein itself is used, including insulin, calcitonin, erythropoietin and other peptides;

(ee) any vitamin used in the treatment of any disease, or used in foods, nutritional supplements or food additives as a way of providing the vitamin effectively;

(ff) any antioxidant used in the management of any disease, but especially for those diseases in which antioxidants may be especially beneficial including cardiovascular diseases, cancer and inflammatory disorders and any antioxidant used as a food or other preservative or as a component of a food, food additive or nutritional supplement, (gg) any porphyrin chlorin or bacteriochlorin-based drug especially tetralis (hydroxy phenyl) derivatives thereof used in photodynamic therapy of cancers.

Ease of Synthesis

Synthesis of Trielycerides

The following considers the advantages of use of 1,3-propane diol compared in particular to triglycerides.

Specifically, it is proposed that 1,3-propane diol be used in place of glycerol in the esterification of fatty acids, especially where only one type of fatty acid (e.g. gamma-linolenic acid) is to be attached to the three-carbon chain "backbone". Although diesters and triglycerides are chemically very similar, the manufacture of di-esters can be carried out under very mild conditions, and in a matter of hours. To manufacture triglycerides, either harsh conditions are required, or fatty acid chlorides must be used, or biocatalysts (which require reaction times of several days) are necessary.

A summary of triglyceride synthesis methods is: chemical reaction with metals, metal-chlorides, or organic acids as catalyst; use of fatty-acid chlorides; use of immobilised enzymes.

All processes using acids, metals, or metal chlorides as catalysts are very similar and share a common list of advantages and disadvantages. Many of the problems are inherent to the methods, i.e; acidic conditions and high temperatures (140° C. to 180° C.). The p-TSA method probably exhibits the least problems, as this is carried out under the mildest conditions (140° C.). Reaction of glycerol with fatty acid chlorides is done under "cold" conditions, but toxic gases are evolved and the reaction can go out of control if not monitored carefully. This method also suffers from the fact that the fatty acid chlorides themselves must first be manufactured; this additional step reduces the overall efficiency of the process. A particular family of enzymes, the lipases, can be used to catalyse the esterification reaction under very mild conditions (e.g. at 60° C.), and are probably the catalysts of choice when polyunsaturated fatty acids are being used. However, most enzymes interact most effectively with the 1- and 3-positions of glycerol. Addition of fatty acid to the 2-position is slow, and often dependant upon "acyl migration", i.e. a fatty acid must first be attached to the 1- or 3-position, and then migrate to the 2-position, where it remains attached. Thus, triglyceride synthesis reactions which are catalysed by enzymes can take days to approach completion.

In theory, the same methods can be applied to the esterification of 1,3-propanediol as can be applied to glycerol. However, when it is considered that enzymes catalyse preferentially the addition of fatty acids to the 1- and 3-positions of glycerol, it is clear they should be particularly effective when used to make diesters. This is indeed the case, with reactions being completed in a matter of hours and at temperatures which are even lower (e.g. 45° C. to 60° C.) than those required for triglyceride synthesis. After four hours free fatty acid can be absent, and after eight hours the yield of diester can be in excess of 95%, the balance being monoester.

A further complexity with specific triglyceride syntheses is the presence within glycerol of both primary and secondary hydroxyl groups and a prochiral centre at the central carbon atoms. These problems may be solved by the use of carefully selected protecting groups and by chiral synthesis. However, this results in multistep syntheses with decreasing yield and increasing impurity levels at each step. In contrast, however, 1,3-propane diol possesses only primary hydroxyl groups and no prochiral centres. The synthesis is consequently reduced to two steps maximum with improved overall yield and decreased impurity levels.

In summary, the reaction which prepares diesters from polyunsaturated fatty acids and 1,3-propane diol is faster, and can be carried out under much milder conditions, than can the corresponding triglyceride synthesis. This leads to a more economical and less wasteful production process and minimises the risk of reactants or products becoming altered or degraded during processing.

Formulations

The compounds may be formulated in any way appropriate and which is known to those skilled in the art of preparing pharmaceuticals, skin care products or foods. They may be administered orally, enterally, topically, parenterally (subcutaneously, intramuscularly, intravenously), rectally, vaginally or by any other appropriate route.

Like triglycerides, the 1,3-propane diol diesters, especially those containing two fatty acids, may be readily emulsified using phospholipid or particularly galactolipid emulsifiers. Such emulsions are particularly useful for administration via oral, enteral and intravenous routes.

For example, fatty acid (UFA) diesters occur as free flowing oils and therefore can be formulated as follows:

1. Preparation of 20% Emulsion of Diester of GLA and EPA with 1,3-Propane Diol

Oral emulsions were prepared by high-pressure homogenisation. The particle size distributions and the zeta potential of the resulting emulsions were determined by dynamic light scattering at room temperature. The particle size measurements were carried out at room temperature (Zetasizer 4 Malvern Instruments Limited).

An oil-in-water emulsion (batch size 200 g) was prepared containing the following ingredients:

| Ingredients | % |
|---|---|
| Emulsifier (Galactolipid)* | 2.00 |
| Diester (GLA-EPA) | 20.00 |
| Ascorbyl Palmitate (AP) | 0.02 |
| Vitamin E | 0.5 |
| Water | 100.00 |

The emulsifier-galactolipid was dispersed in the diester and Vitamin E, AP and water were mixed. The oil phase was added to the aqueous phase under a high shear mix (Ultraturrax) at speed 4, for a few minutes. This pre-emulsion was then homogenised at 80 MPA and at 50° C. for 6 cycles (mini-Lab 8.30 H; APV Rannie AS, Denmark). The emulsion formed has an average droplet size of 230 nm.

Anti-microbial preservatives—potassium sorbate, and flavour, can also be added to the above oral emulsion.

2. Preparation of Intravenous 20% Emulsion of Diester of GLA and EPA with 1,3-Propane Diol In a similar manner, 200 g of an oil-in-water emulsion was prepared containing the following ingredients:

| Ingredients | % |
|---|---|
| Emulsifier | 2.0 |
| Diester (GLA-EPA) | 20.0 |
| Glycerol | 2.0 |
| Water add to | 100.00 |

The above emulsion, homogenised for 6 minutes in a high pressure homogeniser had an average droplet size of 211 nm, a zeta potential of −40 mV. These I.V. emulsions can be either filtered through a membrane with a pore size of 0.22 microns or can be autoclaved with change in droplet size.

The doses of the actives to be administered largely range from 1 mg to 200 g per day, preferably 10 mg to 10 g and very preferably 10 mg to 3 g, according to their kind. In the treatment of cancer preferable doses may be in the 2–150 g/day range. They may be administered topically where appropriate in preparations where the actives form from 0.001% to 50% of the topical preparation, preferably 0.05% to 20% and very preferably 0.1% to 10%.

EXAMPLES

Illustrative syntheses of NSAID's linked to fatty acids are given in published EPA-0 675 103 referred to earlier. Illustrative syntheses of the linking of fatty acids, through 1,3-propane diol residues follow, with other generally illustrative material.

Example 1

1,3-(di-z,z,z-Octadeca-6,9,12-trienoyloxy)propane (Diester of GLA with 1,3-Propane Diol)

A solution of 1,3-dicyclohexylcarbodiimide (1.07 g) and 4-(N,N-dimethylamino)pyridine (0.59 g) in methylene chloride (5 ml) was added to a solution of 1,3-dihydroxypropane (0.152 ml) and z,z,z-octadeca-6,9,12-trienoic acid (95%, 1.36 g) in methylene chloride (15 ml). The reaction was stirred at room temperature under nitrogen until it was complete as determined by tlc. Hexane (80 ml) was added to the reaction. The precipitate was removed by filtration and washed thoroughly with hexane. The combined filtrates were concentrated and purified by flash chromatography to yield 1,3-(di-z,z,z-octadeca-6,9,12-trienoyloxy)propane as a pale yellow free flowing oil.

Example 2

1-(z,z,z-Octadeca-6,9,12-trienoyloxy)-3-(z-octadeca-9-enoyloxy)propane (Diester of GLA and Oleic Acid with 1,3-Propane Diol).

Part 1:

A solution of z,z,z-octadeca-6,9,12-trienoic acid (150 g) in methylene chloride (500 ml) was added dropwise to a mixture of 1,3-dihydroxypropane (205 g), 1,3-dicyclohexylcarbodiimide (130 g) and 4-(N,N-dimethylamino)pyridine (87 g) in methylene chloride (2500 ml) at room temperature under nitrogen. When tlc indicated that the reaction had gone to completion the reaction mixture was filtered. The filtrate was washed with dilute hydrochloric acid, water and saturated sodium chloride solution. The solution was dried, concentrated and purified by dry column chromatography to yield 1-(z,z,z-octadeca-6,9,12-trienoyloxy)-3-hydroxypropane as a pale yellow oil.

Part 2:

A solution of 1,3-dicyclohexylcarbodiimide (23.7 g) and 4-(N,N-dimethylamino)pyridine (15.9 g) in methylene chloride (200 ml) was added to a solution of 1-(z,z,z-octadeca-6,9,12-trienoyloxy)-3-hydroxypropane (33.6 g) and z-octadeca-9-enoic acid (30 g) in methylene chloride (400 ml) under nitrogen at room temperature. On completion of reaction as evidenced by tic analysis the solution was diluted with hexane, filtered, concentrated and purified by dry column chromatography to yield 1-(z,z,z-octadeca-6,9,12-trienoyloxy)-3-(z-octadeca-9-enoyloxy)propane as a free flowing pale yellow oil.

Example 3

1-(z,z,z-Octadeca-6,9,12-trienoyloxy)-3-(z,z,z,z,z-eicosa-5,8,11,14,17-pentaenoyloxy)propane (Diester of GLA and EPA with 1,3-Propane Diol).

Prepared as in Example 2, Part 2 but replacing z-octadeca-9-enoic acid with z,z,z,z,z-eicosa-5,8,11,14,17-pentaenoic acid. Chromatography yielded 1-(z,z,z-octadeca-6,9,12-trienoyloxy)-3-(z,z,z,z,z-eicosa-5,8,11,14,17-pentaenoyloxy)propane as a pale yellow oil.

Example 4

1,3-di(z,z,z-Octadeca-6,9,12-trienoyloxy)propane (Diester of GLA with 1,3-Propane Diol).

Prepared as in Example 2, Part 2 but replacing z-octadeca-9-enoic acid with z,z,z-octadeca-6,9,12-trienoic acid. Chromatography yielded 1,3-(di-z,z,z-octadeca-6,9,12-trienoyloxy)propane as a pale yellow oil.

Example 5

(±)-1-(1,2-Dithiolane-3-pentanoyloxy)-3-(z,z,z-octadeca-6,9,12-trienoyloxy)propane (Diester of Lipoic Acid and GLA with 1,3-Propane Diol)

A mixture of 1,3-dicyclohexylcarbodiimide (720 mg, 3.45 mmol) and 4-(N,N-dimethylamino)pyridine (480 mg, 3.98 mmol) in tert-butyl methyl ester (15 ml) was added to a mixture of lipoic acid (645 mg, 3.12 mmol) and 1-(z,z,z-octadeca-6,9,12-trienoyloxy)-3-hydroxypropane (1 g, 3 mmol) in tert-butyl methyl ether (30 ml). The mixture was stirred at room temperature under nitrogen for 5 h, the progress of reaction being monitored by tic (40% ethyl acetate/hexane). On completion the mixture was filtered, concentrated and purified by flash chromatography (hexane, 2% ethyl acetate/hexane, 5% ethyl acetate/hexane and finally 10% ethyl acetate/hexane) to yield (±)-1-(1,2-dithiolane-3-pentanoyloxy)-3-(z,z,z-octadeca-6,9,12-trienoyloxy)propane as a viscous yellow oil.

Example 6

1-([Z]-5-Fluoro-2-methyl-1-[4-{methylsulfinyl}benzylidenedindene-3-acetyloxy)-3-(z,z,z-octadeca-6,9,12-trienoyloxy)propane (Diester of Sulindac and GLA with 1,3-Propane Diol)

A solution of 1,3-dicyclohexylcarbodiimide (720 mg, 3.45 mmol) in tert butyl methyl ether (30 ml) was added to a mixture of sulindac (1.12 g, 3.15 mmol), 4-(N,N-dimethylamino)pyridine (480 mg, 3.9 mmol) and 1-(z,z,z-octadeca-6,9,12-trienoyloxy)-3-hydroxypropane (1 g, 3 mmol) in tert-butyl methyl ether (15 ml). The mixture was stirred at room temperature under nitrogen for 5 h, the progress of reaction being monitored by tlc (40% ethyl acetate/hexane). On completion the mixture was filtered, concentrated and purified by flash chromatography (40% ethyl acetate/hexane, then 50% ethyl acetate/hexane and finally 60% ethyl acetate/hexane) to yield 1-([Z]-5-fluoro-2-methyl-1-[4-{methylsulfinyl}benzylidene]indene-3-acetyloxy)-3-(z,z,z-octadeca-6,9,12-trienoyloxy)propane as a waxy yellow solid.

Example 7

1-([R]-3-Acetoxy-4-[(trimethylammonio]butyroyloxy)-3-(z,z,z-octadeca-6,9,12-trienoyloxy)propane (Diester of Acetyl Carnitine and GLA with 1,3-Propane Diol).

Freshly distilled thionyl chloride (1.5 ml) was slowly added to (R)-acetyl carnitine (1 g.) in a pear shaped flask. Care was taken to contain the reagents at the bottom of the flask until a clear solution resulted. After 4 hours at room temperature excess thionyl chloride was removed under reduced pressure (keeping the flask temperature less than 30° C.). This yielded the acid chloride as a highly hydroscopic white solid which was used immediately without further purification. To the flask were added 1-(z,z,z-octadeca-6,9,12-trienoyloxy)-3-hydroxypropane (1.4 g, 4.17 mmol) and dry THF (4 ml). The mixture was allowed to stand overnight at room temperature. Tlc analysis (40% ethyl acetate/hexane) indicated that the reaction had gone to completion. The reaction mixture was added dropwise to hexane (250 ml) with vigorous stirring. A fine off white precipitate formed which was collected by centrifugation. On removal of the supernatant the solid was resuspended in hexane and centrifuged. The hexane washing procedure was carried out once more to yield 1-([R]-3-acetoxy-4-[trimethylammonio]butyroyloxy)-3-(z,z,z-octadeca-6,9,12-trienoyloxy)propane.

Example 8

1-(3,3-Dimethyl-7-oxo-6-((phenoxyacetyl)amino]4-thia-1-azabicyclo[3.2.0]heptan-2-oyloxy)-3-(z,z,z-octadeca-6,9,12-trienoyloxy)propane.

(Diester of Penicillin V and GLA with 1,3-Propane Diol).

A mixture of penicillin V (1 g, 2.9 mmol), 1-(z,z,z-octadeca-6,9,12-trienoyloxy)-3-hydroxypropane (860 mg, 2.6 mmol), 1,3-dicyclohexylcarbodiimide (620 mg, 3 mmol) and 4-(N,N-dimethylamino)pyridine (catalytic amount) in dichloromethane (30 ml) was stirred overnight at room temperature. The reaction mixture was diluted with hexane (50 ml), filtered and concentrated to dryness. The residue was washed with hexane (3×50 ml) to remove unreacted 1-(z,z,z-octadeca-6,9,12-trienoyloxy)-3-hydroxypropane. The semi-solid residue was disolved in diethyl ether (150 ml), washed with water (100 ml) and dried. The ether solution was diluted with hexane (125 ml) and the solution filtered through a bed of silica (4 cm×4 cm). The filtrate was concentrated, yielding 1-(3,3-dimethyl-7-oxo-6([phenoxyacetyl)amino]-4-thia-1-azabicyclo[3.2.0]heptan-2-oyloxy)-3-(z,z,z-octadeca-6,9,12-trienoyloxy)propane as a viscous colourless oil.

Example 9

1-(z,z,z-Octadeca-6,9,12-trienoyloxy)-3-(I-(4-chlorobenzoyl)-5-methoxy-2-methyl-indole-3-acetyloxy)propane.

(Diester of Indomethacin and GLA with 1,3-Propane Diol).

A solution of 1,3-dicyclohexylcarbodiimide (58 g, 0.28 mol) and 4-(N,N-dimethylamino)pyridine (37.9 g, 0.31 mol) in methylene chloride (800 ml) was added with stirring to a solution of 1-(z,z,z-octadeca-6,9,12-trienyloxy)-3-hydroxypropane (79.5 g, 0.24 mol) and indomethacin (93.2 g, 0.26 mol) in methylene chloride (400 ml) at room temperature under nitrogen. Stirring was continued for 3 h. The mixture was filtered, concentrated and purified by dry column chromatography (ethyl acetate/hexane). The product fractions were pooled and concentrated, yielding 1-(z,z,z-octadeca-6,9,12-trienyloxy)-3-(1-(3-chlorobenzoyl)-5-methoxy-2-methyl-indole-3-acetyloxy)propane as a bright yellow viscous oil.

Example 10

1-(z,z,z-Octadeca-6,9,12-trienoyloxy)-3-(2-pyrrolidine carboxy)propane (Diester of Proline and GLA with 1,3-Propane Diol).

Part 1:

A solution of 1,3-dicyclohexylcarbodiimide (674 mg, 3.3 mmol) and and 4-(N,N-dimethylamino)pyridine (472 mg, 3.9 mmol) in methylene chloride (20 ml) was added with stirring to a solution of 1-(z,z,z-octadeca-6,9,12-trienyloxy)-3-hydroxypropane (1 g, 2.97 mmol) and N-tBOC-proline (671 mg, 3.12 mmol) in methylene chloride (20 ml) at room temperature under nitrogen. Stirring was continued for 7 h and the mixture stored overnight at 0° C. The mixture was filtered and purified by column chromatography (methanol/methylene chloride) to yield 1-(z,z,z-octadeca-6,9,12-trienoyloxy)-3-(N-tBOC-2-pyrrolidine carboxy)propane as a yellow oil.

Part 2:

The protected product was dissolved in 10% v/v anisole/trifluoroacetic acid (10 ml) and left at room temperature under nitrogen for 30 minutes. After tlc analysis indicated that deprotection was complete, the mixture was purified by column chromatography (8% methanol/42% methylene chloride/50% ethyl acetate) to yield 1-(z,z,z-octadeca-6,9,12-trienyloxy)-3-(2-pyrrolidine carboxy)propane as a viscous orange oil.

Example 11

1-(z,z,z-Octadeca-6,9,12-trienoyloxy)-3-(2-amino-3-indolylpropanoyloxy)propane (Diester of Tryptophan and GLA with 1,3-Propane Diol).

Part 1:

A solution of 1,3-dicyclohexylcarbodiimide (674 mg, 3.3 mmol) and and 4-(N,N-dimethylamino)pyridine (472 mg, 3.9 mmol) in methylene chloride (20 ml) was added with stirring to a solution of 1-(z,z,z-octadeca-6,9,12-trienyloxy)-3-hydroxypropane (1 g, 2.97 mmol) and N-TSOC-tryptophan (950 mg, 3.12 mmol) in methylene chloride (20 ml) at room temperature under nitrogen. Stirring was continued for 7 h and the mixture stored overnight at 0° C. The mixture was filtered and purified by column chromatography (methanol/methylene chloride) to yield 1-(z,z,z-octadeca-6,9,12-trienoyloxy)-3-(N-tBOC-2-amino-3-indolylpropanoyloxy)propane as a yellow oil.

Part 2:

The protected product was dissolved in 10% v/v anisole/trifluoroacetic acid (6.1 ml) and left at room temperature under nitrogen for 15 minutes. After tlc analysis indicated that deprotection was complete, the mixture was purified by column chromatography (8% methanol/42% methylene chloride/50% ethyl acetate) to yield 1-(z,z,z-octadeca-6,9,12-trienyloxy)-3-(2-amino-3-indolylpropanoyloxy)propane as a viscous red wax.

Example 12

1-(z,z,z-Octadeca-6,9,12-trienoyloxy)-3-(α-amino-β-phenyl-propionyloxy)propane (Diester of Phenylalanine and GLA with 1,3-Propane Diol).

Part 1:

A solution of 1,3-dicyclohexylcarbodiimide (1.77 g, 8.57 mmol) and and 4-(N,N-dimethylamino)pyridine (1.24 g, 10.13 mmol) in methylene chloride (30 ml) was added with stirring to a solution of 1-(z,z,z-octadeca-6,9,12-trienyloxy)-3-hydroxypropane (2.62 g, 7.79 mmol) and N-TBOC-phenylalanine (2.17 g, 8.18 mmol) in methylene chloride (30 ml) at room temperature under nitrogen. Stirring was continued for 7 h and the mixture stored overnight at 0° C. The mixture was filtered and purified by column chromatography (methanol/methylene chloride) to yield 1-(z,z,z-octadeca-6,9,12-trienoyloxy)-3-(N-tBOC-α-amino-β-phenyl-propionyloxy)propane as a yellow oil.

Part 2:

The protected product was dissolved in 10% v/v anisole/trifluoroacetic acid (17 ml) and left at room temperature under nitrogen for 30 minutes. After tlc analysis indicated that deprotection was complete, the mixture was purified by column chromatography (8% methanol/42% methylene chloride/50% ethyl acetate) to yield 1-(z,z,z-octadeca-6,9,12-trienyloxy)-3-(α-amino-β-phenyl-propionyloxy)propane as a viscous yellow oil.

Example 13

1-(z,z,z-Octadeca-6,9,12-trienoyloxy)-3-(4-aminobutanoyloxy)propane (Diester of GABA and GLA with 1,3-Propane Diol).

Part 1:

A solution of 1,3-dicyclohexylcarbodiimide (0.84 g, 4.06 mmol) and and 4-(N,N-dimethylamino)pyridine (0.59 g, 4.79 mmol) in methylene chloride (10 ml) was added with stirring to a solution of 1-(z,z,z-octadeca-6,9,12-trienyloxy)-3-hydroxypropane (1.24 g, 3.96 mmol) and N-tBOC-GABA (0.75 g, 3.69 mmol) in methylene chloride (15 ml) at room temperature under nitrogen. Stirring was continued for 7 h and the mixture stored overnight at 0° C. The mixture was filtered and purified by column chromatography (ethyl acetate/hexane) to yield 1-(z,z,z-octadeca-6,9,12-trienoyloxy)-3-(N-tBOC-4-amino butanoyloxy)propane as a colourless oil.

Part 2:

The protected product was dissolved in 10% v/v anisole/trifluoroacetic acid (10.5 ml) and left at room temperature under nitrogen for 30 minutes. After tlc analysis indicated that deprotection was complete, the mixture was purified by column chromatography (8% methanol/42% methylene chloride/50% ethyl acetate) to yield 1-(z,z,z-octadeca-6,9,12-trienyloxy)-3-(4-amino butanoyloxy)propane as a yellow oil.

Example 14

3,3'-thio-di-(1-Propionyloxy-(3-(z,z,z-octadeca-6,9,12-trienoyloxy)-propane))

(Bis Diester of GLA and 1,3-Propane Diol with 3,3'-Thiodipropionic Acid).

A solution of 1,3-dicyclohexylcarbodiimide (660 mg, 3.22 mmol) and 4-(N,N-dimethylamino)pyridine (445 mg, 3.64 mmol) in methylene chloride (10 ml) was added with stirring to a solution of 1-(z,z,z-octadeca-6,9,12-trienyloxy)-3-hydroxypropane (940 mg, 2.8 mmol) and 3,3'-thiodipropionic acid (250 mg, 1.4 mmol) in methylene chloride (30 ml) at room temperature under nitrogen. Stirring was continued for 4 h. The mixture was diluted with hexane (50 ml), filtered, concentrated and purified by flash chromatography (ethyl acetate/hexane). The product fractions were pooled and concentrated yielding 3,3'-thio-di-(1-propionyloxy-(3-(z,z,z-octadeca-6,9,12-trienoyloxy)-propane)) as a colourless oil.

Example 15

1-(1-(z,z,z-Octadeca-6,9,12-trienoyloxy)-3-propyl)4-(z,z,z-octadeca-6,9,12-trienyl)butane-1,4-dioate (Diester of (GLM Monoester with 1,3-Propane Diol) and GLA Alcohol with Succinic Acid).

Part 1:

A mixture of 1-(z,z,z-octadeca-6,9,12-trienyloxy)-3-hydroxypropane (10 g, 30 mmol) and succinic anhydride (3 g, 30 mmol) in dry THF (100 ml) was stirred at room temperature until a clear solution resulted. This solution was cooled to 0° C. and a solution of 1,8-diazabicyclo[5.4.0]undec-7-ene (4.5 ml, 30 mmol) in dry THF (50 ml) added dropwise to it. After 3 h, tlc analysis indicated that most of the monoester had reacted. A few more crystals of succinic anhydride were added and stirring continued for a further 30 min. The reaction mixture was diluted with diethyl ether (250 ml) and washed with 2M hydrochloric acid (2×250 ml), water (250 ml) and brine (250 ml). It was then dried (sodium sulfate) and concentrated to dryness. The material was used without any further purification.

Part 2:

Oxalyl chloride (3.9 ml, 45 mmol) was added to a solution of the product from part 1 (13 g, 30 mmol) in methylene chloride (75 ml). The mixture was stirred at room temperature under nitrogen for 2 h and concentrated to dryness. Hexane (75 ml) was added and the mixture concentrated to dryness. This process was repeated with two further portions of hexane (75 ml ea.). The material was used without any further purification.

Part 3:

A solution of the acid chloride prepared in part 2 (1 g 2.2 mmol) in methylene chloride (10 ml) was added dropwise to a solution of z,z,z-octadeca-6,9,12-trienol (635 mg, 2.4 mmol), triethylamine (1 ml, 7.2 mmol) and 4-(N,N-dimethylamino)pyridine (cat. amount) in methylene chloride (20 ml) at room temperature. On completion of reaction, the mixture was concentrated and purified by flash chromatography (ethyl acetate/hexane) to yield 1-(1-(z,z,z-octadeca-6,9,12-trienoyloxy)-3-propyl)-4-(z,z,z-octadeca-6,9,12-trienyl)butane-1,4-dioate as a colourless oil.

Example 16

1-(2,3,5-Triiodobenzoyloxy)-3-(z,z,z-octadeca-6,9,12-trienoyloxy)propane (Diester of 2,3,5-(Triiodobenzoic Acid and GLA with 1,3-Propane Diol)

2,3,5-Triiodobenzoyl chloride (1.54 g, 3.08 mmol) was added to a mixture of 1-(z,z,z-octadeca-6,9,12-trienoyloxy)-3-hydroxypropane (1 g, 2.97 mmol) and triethylamine (1 ml) in methylene chloride (80 ml) and the resulting mixture stirred overnight at room temperature under nitrogen. The mixture was concentrated and purified by flash chromatography (ethyl acetate/hexane) to yield 1-(2,3,5-triiodobenzoyloxy)-3-(z,z,z-octadeca-6,9,12-trienoyloxy)propane.

Example 17

(±)-1-(1,2-Dithiolane-3-pentanoyloxy)-3-(z,z,z,z,z,z-docosa-4,7,10,3,16,19-hexaenoyloxy)propane (Diester of DHA and Liptic Acid with 1,3-Propane Diol)

Part 1:

A solution of z,z,z,z,z,z-docosa-4,7,10,13,16,19-hexaenoic acid (6.4 g, 19.5 mmol) in methylene chloride (225 ml) was added dropwise to a solution of 1,3-propane diol (7.5 g, 99 mmol), 1,3-dicyclohexylcarbodiimide (4.65 g, 20 mmol) and 4-(N,N-dimethylamino)pyridine (2.1 g, 17 mmol) in methylene chloride (225 ml) at −10° C. The reaction mixture was stirred overnight, warming up to room temperature. The reaction was filtered, concentrated and purified by flash chromatography (ethyl acetate/hexane) to yield 1-(z,z,z,z,z,z-docosa-4,7,10,13,16,19-hexaenoyloxy)-3-hydroxypropane as a pale yellow oil.

Part 2:

A solution of 1,3-dicyclohexylcarbodiimide (720 mg, 3.45 mmol) and 4-(N,N-dimethylamino)pyridine (480 mg, 3.9 mmol) in methylene chloride (30 ml) was added to a mixture of 1-(z,z,z,z,z,z-docosa-4,7,10,13,16,19-hexaenoyloxy)-3-hydroxypropane (1.16 g, 3 mmol) and lipoic acid (645 mg, 3.12 mmol) and methylene chloride (15 ml). After 2.5 h at room temperature under nitrogen the mixture was filtered, concentrated and purified by flash chromatography (ethyl acetate hexane) to yield (±)-1-(1,2-dithiolane-3-pentanoyloxy)-3-(z,z,z,z,z,z-docosa-4,7,10,13,16,19-hexaenoyloxy)propane as a yellow oil.

Example 18

Methyl-di(z,z,z-octadeca-6,9,12-trienoyloxypropyl)-phosphate

Phosphotnester of 2 Molecules of 3-Hydroxypropyl Ester of GLA and 1 Molecule of Methanol)

Part 1:

Triethylamine (3.74 ml, 26.8 mmol) was added dropwise to a cooled (0° C.) solution of freshly distilled phosphorus oxychloride (2.74 g, 17.9 mmol) in anhydrous THF (15 ml). To this mixture was added dropwise a solution of 1-(z,z,z-octadeca-6,9,12-trienoyloxy)-3-hydroxypropane (5 g, 14.9 mmol) in anhydrous THF (15 ml). The temperature was kept at less than 10° C. throughout and the reaction kept under an atmosphere of nitrogen. Tlc analysis after 15 min. indicated complete disappearance of starting material. The mixture was filtered and concentrated. Toluene (50 ml) was added and the mixture concentrated. A further portion of toluene (50 ml) was added and removed.

Part 2:

A solution of 1-(z,z,z-octadeca-6,9,12-trienoyloxy)-3-hydroxypropane (3 g, 9 mmol) in anhydrous THF (10 ml) was added dropwise to a solution of crude phosphochloridate (7.5 mmol) (half of the batch prepared in part 1 above) and triethylamine (3.2 ml, 22.5 mmol) in anhydrous THF (20 ml) at room temperature under nitrogen. The reaction was stored for 3 days at less than 10° C. Methanol (15 ml) was added and the reaction kept at room temperature until tlc indicated complete reaction of the phoshorochloridate to form the desired phosphotriester. Purification by flash chromatography (ethyl acetate/hexane) yielded methyl-di(z,z,z-octadeca-6,9,12-trienoyloxypropyl)-phosphate as a colourless oil.

Example 19

Di(z,z,z-Octadeca6,9,12-trienoyloxypropyl) phosphate.

(Phosphodiester of 2 Molecules of 3-Hydroxyproypl Ester of GLA)

Lithium bromide (104 mg, 1.13 mmol) in methyl ethyl ketone (1 ml) was added to a solution of methyl-di(z,z,z-octadeca-6,9,12-trienoyloxypropyl)-phosphate (0.85 g, 1.13 mmol) (prepared as in example 18) in methyl ethyl ketone (1 ml) and the mixture was heated under reflux for 1 h. After cooling, the mixture was dissolved in diethyl ether (3 ml) and extracted with water (3 ml). Emulsions formed were broken by the addition of a few drops of methanol. The organic layer was separated, dried (sodium sulfate), concentrated and purified by flash chromatography (methanol/chloroform) to yield di(z,z,z-octadeca-6,9,12-trienoyloxypropyl)phosphate as a waxy white solid.

Example 20

(2-Aminoethyl)-(z,z,z-octadeca-6,9,12-trienoyloxypropyl)phosphate (Phosphodiester of Ethanolamine and 3-Hydroxypropyl Ester of GLA)

Part 1:

A mixture of ethanolamine (0.5 ml, 8.25 mmol) and triethylamine (4.2 ml, 30 mmol) in anhydrous THF (20 ml) was added to a solution of crude phosphochloridate (7.5 mmol) (half of the batch prepared in example 18, part 1 above) in anhydrous THF (20 ml), keeping the temperature less than 10° C. Progress of the reaction was monitored by tlc. The mixture was stored for 3 days at less than 5° C. After that time it was filtered, concentrated, diluted with hexane (50 ml) and reconcentrated.

Part 2:

The product obtained from part 1 was dissolved in isopropanol (100 ml), acetic acid (10 ml) and water (40 ml) and the solution allowed to stand under nitrogen at room temperature. When tic indicated that the reaction had gone to completion the mixture was concentrated and partitioned between acetonitrile (50 ml) and hexane (50 ml). The hexane layer was separated, concentrated and purified by flash chromatography (methanol/chloroform 1 water). The pure fractions were pooled and concentrated. Addition of ethyl acetate crashed out (2-aminoethyl)-(z,z,z-octadeca-6,9,12-trienoyloxypropyl)phosphate as a waxy cream coloured solid which was collected by centrifugation.

Example 21

(z,z,z-Octadeca-6,9,12-trienoyloxypropyl)-(2-(N,N,N-trimethylammonium)ethyl)phosphate (Phosphodiester of Choline and 3-Hydroxypropyl Ester of GLA).

Part 1:

A solution of 2-chloro-1,3,2-dioxaphospholane-2-oxide (430 mg, 3.4 mmol) in toluene (5 ml) was added to a cooled (0° C.) solution of 1-(z,z,z-octadeca-6,9,12-trienoyloxy)-3-hydroxypropane (1 g, 2.98 mmol) and tnethylamine (0.57 ml, 4.1 mmol) in toluene (45 ml). The mixture was stirred overnight, warming up to room temperature. Tlc analysis indicated that the reaction had not gone to completion. Further portions of triethylamine (0.3 ml) and 2-chloro-1,3,2-dioxaphospholane-2-oxide (200 mg) (as a solution in toluene (5 ml)) were added and the reaction allowed to continue for a further overnight period. After that time tic indicated complete reaction and the mixture was concentrated.

Part 2:

The crude product from part 1 was dissolved in acetonitrile (60 ml). A quarter of this solution (15 ml) and trimethylamine (10 ml) were heated in a sealed tube at 60° C. for 5 h (CAUTION). The reaction was cooled and concentrated under a stream of nitrogen to yield (z,z,z-octadeca-6,9,12-trienoyloxypropyl)-(2-(N,N,N-trimethylammonium)ethyl) phosphate.

Example 22

(z,z,z-Octadeca-6,9,12-trienoyloxypropyl)phosphate (Phosphomonoester of 3-Hydroxypropyl Ester of GLA).

A solution of 1-(z,z,z-octadeca-6,9,12-trienoyloxy)-3-hydroxypropane (1.95 g, 5.8 mmol), pyridine (1.4 ml, 17.3 mmol) and anhydrous THF (15 ml) was added dropwise with stirring to a cooled (0° C.) solution of phosphorus oxychloride (1.02 g, 6.6 mmol) in anhydrous THF (5 ml) and the resultant mixture was kept at 0° C. for 3 h. Aqueous sodium bicarbonate (10% w/w, 10 ml) was added to the reaction mixture. After stirring for 20 min. the mixture was poured into ice/water (30 ml) and the solution acidified to pH 1 by the dropwise addition of 2M hydrochloric acid. The mixture was extracted with diethyl ether (2×30 ml). The ether extracts were combined, dried and concentrated. The resultant oil was azeotroped with dry pyridine to yield (z,z,z-octadeca-6,9,12-trienoyloxypropyl)phosphate as a viscous yellow oil.

Example 23

Methyl-(z,z,z-octadeca-6,9,12-trienoyloxypropyl)-(α-tocopheryl)phosphate (Phosphotriester of α-Tocopherot, Methanol and 3-Hydroaypropyl Ester of GLA).

Part 1:

Triethylamine (7.5 ml) was added to a solution of freshly distilled phosphorus oxychloride (1.26 g, 8.25 mmol) in anhydrous THF (7.5m) at 0° C. After 15 min. a solution of 1-(z,z,z-octadeca-6,9,12-trienoyloxy)-3-hydroxypropane (2.5 g, 7.5 mmol) in anhydrous THF (7.5 ml) was added dropwise over a period of 30 min. at 0° C. Stirring at this temperature was continued for 30 min. after the end of addition. α-Tocopherol (3.23 g, 7.5 mmol) in anhydrous THF (5 ml) was added dropwise at 10° C. and the resultant mixture was then stirred at 10° C. for 1 h and then overnight, warming up to room temperature.

Part 2:

One quarter of the mixture prepared in part 1 above, triethylamine (0.8 ml, 6 mmol) and methanol (10 ml) were stirred overnight under nitrogen at room temperature. The reaction mixture was concentrated and partitioned between ethyl acetate (30 ml) and water (20 ml) with sodium chloride and methanol being added to break the emulsion. The ethyl acetate layer was dried, concentrated and purified by flash chromatography (chloroform) to yield methyl-(z,z,z-octadeca6,9,12-trienoyloxypropyl)-(α-tocopheryl) phosphate.

Example 24

(z,z,z-Octadeca-6,9,12-trienoyloxypropyl)-(α-tocopheryl)phosphate (Phosphodiester of α-Tocopherol and 3-Hydroxypropyl Ester of GLA).

Triethylamine (2 ml) and water (5 ml) were added to one quarter of the reaction mixture as prepared in example 23, part 1. The mixture was stirred under nitrogen in an ice bath for 1 h, acidified to pH 1 with 2M hydrochloric acid and extracted into ethyl acetate (20 ml) and methanol (5 ml). The extract was dried concentrated and purified by flash chromatography (chloroform) to yield (z,z,z-octadeca-6,9,12-trienoyloxypropyl)-(α-tocopheryl)phosphate.

Example 25

1-(z,z,z-Octadeca-6,9,12-trienoyloxy)-5-(z,z,z,z,z-eicosa-5,8,11,14,17-pentaenoyloxy)pentane (Diester of GLA and EPA with 1,5-Pentane Diol).

Part 1:

z,z,z-Octadeca-6,9,12-trienoyl chloride (2 g) was added dropwise to a solution of 1,5-dihydroxypentane (3.5 g), triethylamine (0.94 ml) and 4-(N,N-dimethylamino)pyridine (0.2 g) in methylene chloride (50 ml) with stirring at 0° C. under nitrogen. On completion of reaction as evidenced by tic the reaction mixture was washed with dilute hydrochloric acid and water, dried and purified by column chromatography yielding 1-(z,z,z-octadeca-6,9,12-trienoyloxy)-5-hydroxypentane as a pale yellow oil.

Part 2:

As for Example 2, Part 2 but replacing 1-(z,z,z-octadeca-6,9,12-trienoyloxy)-3-hydroxypropane with 1-(z,z,z-octadeca-6,9,12-trienoyloxy)-5-hydroxypentane and z-octadeca-9-enoic acid with z,z,z,z,z-eicosa-5,8,11,14,17-pentaenoic acid. Chromatography yielded 1-(z,z,z-octadeca-6,9,12-trienoyloxy)-5-(z,z,z,z,z-eicosa-5,8,11,14,17-pentaenoyloxy)pentane as a pale yellow oil.

Example 26

1-(z,z,z-Octadeca-6,9,12-trienoyloxy)-4-(z,z,z,z,z-eicosa-5,8,11,14,17-pentaenoyloxy)benzene (Diester of GLA and EPA with 1,4-Dihydroxybenzene).

Prepared as in Example 25, Parts 1 and 2 but replacing 1,5-dihydroxypentane with 1,4-dihydroxybenzene in Part 1 and replacing methylene chloride with tetrahydrofuran as the solvent in Part 1. Chromatography yielded 1-(z,z,z-octadeca-6,9,12-trienoyloxy)-4-(z,z,z,z,z-eicosa-5,8,11,14,17-pentaenoyloxy)benzene as a pale yellow oil.

Example 27

1,4-di(z,z,z-Octadeca-6,9,12-trienyl)-butane-1,4-dioate (Diester of GLA Alcohol with Succinic Acid)

Part 1:

A solution of 1,8-diazabicyclo[5.4.0]undec-7-ene (0.54 ml) in dry tetrahydrofuran (10 ml) was added dropwise to a cooled (0° C.) solution of z,z,z-octadeca-6,9,12-trienol (1 g) and succinic anhydride (0.36 g) in dry tetrahydrofuran (20 ml). On completion of reaction as evidenced by tlc, the reaction mixture was diluted with diethyl ether and washed with dilute hydrochloric acid, water and brine. The organic layer was dried, concentrated and used directly in the second part of the reaction.

Part 2:

A solution of 1,3-dicyclohexylcarbodiimide (0.83 g) and 4-(N,N-dimethylamino)pyridine (0.55 g) in methylene chloride (20 ml) was added to a solution of 1-(z,z,z-octadeca-6,9,12-trienyl)-butane-1,4-dioate (1.32 g) and z,z,z-octadeca-6,9,12-trienol (0.98 g) in methylene chloride (40 ml). On completion, as evidenced by tlc analysis, the reaction mixture was diluted with hexane, filtered, concentrated and purified by chromatography to yield 1,4-di(z,z,z-octadeca-6,9,12-trienyl)-butane-1,4-dioate as a pale yellow oil.

Example 28

2-(2-Methyl-5-nitroimidazolyl)ether-z,z,z-octadeca-6,9,12-trienoate (Ester of Metronidazole with GLA)

Method A:

To a suspension of metronidazole (206 g) in anhydrous acetonitrile (2300 ml) and anhydrous pyridine (107 ml) was added with stirring at room temperature under nitrogen z,z,z-octadeca-6,9,12-trienoyl chloride (373 g) over a period of 30 mins. Shortly after the addition of the acid chloride a clear solution was formed and stirring was continued for 2 hours. The mixture was allowed to stand overnight and the solvent was removed in vacua (50° C./20 mm Hg). To the residue was added ethyl acetate (1000 ml), any precipitated solid being filtered off. The ethyl acetate solution was washed successively with brine, 2M hydrochloric acid, saturated aqueous sodium bicarbonate solution and finally brine. After drying (sodium sulfate) the solvent was removed to give an orange oil. This material was subjected to dry column chromatography giving 2-(2-methyl-5-nitroimidazolyl) ethyl-z,z,z-octadeca-6,9,12-trienoate as a pale yellow, non-distillable oil.

Method B:

Metronidazole (1.9 g) was suspended in toluene (30 ml) and with stirring the mixture was heated under reflux with a Dean and Stark head for 20 mins. to remove any water present. To the boiling solution was added, under nitrogen, z,z,z-octadeca-6,9,12-trienoyl chloride (2.96 g) dropwise over a period of 20 mins. The mixture was stirred and heated under reflux for a further 2 hours, giving a dark reaction mixture. After cooling, this mixture was subjected to dry column chromatography giving 2-(2-methyl-5-nitroimidazolyl)ethyl-z,z,z-octadeca-6,9,12-trienoate as a pale yellow, non distillable oil.

Example 29

2-(2-Methyl-5-nitroimidazolyl)ethyl-z,z-octadeca-9,12-dienoate (Ester of Metronidazole with LA)

To a suspension of metronidazole (1.9 g) in dry dichloromethane (20 ml) was added successively 4-(N,N-dimethylamino)pyridine (1.22 g), 1,3-dicyclohexylcarbodiimide (2.2 g) and linoleic acid (2.8 g). The mixture was stirred at room temperature overnight. To the reaction was added 2M hydrochloric acid (20 ml) and stirring was continued. After filtration the organic layer was separated, washed with 50% saturated brine and finally with saturated aqueous sodium bicarbonate. The dichloromethane solution was dried (sodium sulfate) and evaporated in vacuo (30° C./20 mm Hg). To the resulting residue was added petrol (bp 30–60° C., 20 ml) and the mixture allowed to stand at room temperature for 2 hours, causing the precipitation of the remaining urea. This was removed by filtration and the filtrate was applied to a dry column giving 2-(2-methyl-5-nitroimidazolyl)ethyl-z,z-octadeca-9,12-dienoate as a pale yellow, non distillable oil.

Example 30

2-(2-Methyl-5-nitroimidazoloyl)ethyl-z,z,z-eicosa-8,11,14-trienoate (Eter of Metronidazole with DGLA)

In a similar manner but replacing the linoleic acid with the requisite amount of z,z,z-eicosa-8,11,14-trienoic acid there is prepared 2-(2-methyl-5-nitroimidazoloyl)ethyl-z,z,z-eicosa-8,11,14-trienoate.

Example 31

2-(2-Methyl-5-nitroimidazoloyl)ethyl-z,z,z,z,z,z-docosa-4,7,10,13,16,19-hexaenoate (Ester of Metronidazole with DHA)

In a similar manner but replacing the linoleic acid with the requisite amount of z,z,z,z,z,z-docosa-4,7,10,13,16,19-hexaenoic acid there is prepared 2-(2-methyl-5-nitroimidazoloyl)ethyl-z,z,z,z,z,z-docosa-4,7,10,13,16,19-hexaenoate.

Example 32

4-[3-[2-(Trifluoromethyl)10H-phenothiazin-10-yl]]-1-piperazineethyl-z,z,z-octadeca-6,9,12-trienoate (Eter of Fluphenazine with GLA)

In a similar manner but replacing, the metronidazole with the requisite amount of the free base of 4-[3-[2-(trifluoromethyl)-10H-phenothiazin-10-yl]]-1-piperazineethanol (fluphenazine) and the linoleic acid with the requisite amount of GLA there is prepared 4-[3-[2-(trifluoromethyl)-10H-phenothiazin-10-yl]]-1-piperazineethyl-z,z,z-octadeca-6,9,12-trienoate.

Example 33

4,4'-(bis z,z,z-Octadeca-6,9,12-trienoylamino) diphenylsulfone (Bis Amide of Dapsone with GLA)

In a similar manner but replacing the metronidazole with the requisite amount of 4,4'-diamino diphenylsulfone (dapsone) and the linoleic acid with the requisite amount of GLA there is prepared 4,4'-(bis z,z,z-octadeca-6,9,12-trienoylamino)diphenylsulfone.

Example 34

N-Methyl-3-phenyl-3[α,α,α-trifluoro-p-tolyl]propyl; z,z,z-Octadeca-6,9,12-trienamide (Amide of Fluoxetine with GLA)

In a similar manner but replacing the metronidazole with the requisite amount of N-methyl-3-phenyl-3[α,α,α-trifluoro-p-tolyl]propylamine (fluoxetine) and the linoleic acid with the requisite amount of GLA there is prepared N-methyl-3-phenyl-3[α,α,α-trifluoro-p-tolyl]propyl-z,z,z-octadeca-6,9,12-trienamide.

Example 35 trans-1-(z,z,z-Octadeca-6,9,12-trienoylamino)-2-phenyl cyclopropane (Amide of Tranylcypromine with GLA)

In a similar manner but replacing the metronidazole with the requisite amount of trans-1-amino-2-phenylcyclopropane (tranylcypromine) and the linoleic acid with the requisite amount of GLA there is prepared trans-1-(z,z,z-octadeca-6,9,12-trienoylamino)-2-phenyl cyclopropane.

Example 36

6-[(Aminophenylacetyl)amino]-3,3-dimethyl-7-oxo-4-thia-1-azabicyclo[3.2.0]heptane-2-carboxylic Acid-z,z,z-octadeca-6,9,12-trienamide (Amide of Ampicillin with GLA)

Triethylamine (0.3 ml) was added to a stirred suspension of ampicillin (0.7 g) in anhydrous DMF (120 ml) under a nitrogen atmosphere. To the resultant clear solution was added z,z,z-octadeca-6,9,12-trienoic acid, N-hydroxysuccinimide ester (0.75 g) while maintaining the reaction at 0–10° C. The reaction was stirred at this temperature for an additional hour before allowing the mixture to stand at room temperature overnight. Tlc analysis (40% THF/hexane) at this point indicated that most of the succinimide ester had reacted. Water (40 ml) was added to the reaction flask and the contents stirred. The solution was then neutralised and extracted with ethyl acetate. The extract was washed with water, dried (sodium sulfate) and concentrated to dryness leaving the crude product as a yellow glass. Trituration with hexane yielded 6-[(aminophenylacetyl) amino]-3,3-dimethyl-7-oxo-4-thia-1-azabicyclo[3.2.0]heptane-2-carboxylic acid-z,z,z-octadeca-6,9,12-trienamide as a yellow powder.

Example 37 z,z,z-Octadeca-6,9,12-trienyl-z,z,z-octadeca-6,9,12-trienoate (Ester of GLA with GLA Alcohol)

1,3-dicyclohexylcarbodiimide (0.82 g) and 4-(N,N-dimethylamino)pyridine (0.48 g) in methylene chloride (5 ml) were added to a solution of z,z,z-octadeca-6,9,12-trienol (0.95 g) and z,z,z-octadeca-6,9,12-trienoic acid (1 g) in methylene chloride (10 ml) with stirring at room temperature under nitrogen. On completion of reaction as evidenced by tlc, hexane was added to the reaction mixture which was subsequently filtered and purified by column chromatography to yield z,z,z-mtadeca-6,9,12-trienyl-z,z,z-octadeca-6,9,12-trienoate as a pale yellow oil.

Example 38 z,z,z-Octadeca-6,9,12-trienyl-z,z,z,z,z-eicosa-5,8,11,14,17-pentaenoate (Ester of EPA with GLA Alcohol)

Prepared as in Example 37 but replacing z,z,z-octadeca-6,9,12-trienoic acid with z,z,z,z,z-eicosa-5,8,11,14,17-pentaenoic acid.

Example 39

2-Methyl-3-(z,z,z,z,z-eicosa-5,8,11,14,17-pentaenoyloxy)-4-formyl-5-(z,z,z,z,z-eicosa-5,8,11,14,17-pentaenoyloxy)methyl pyridine (diEPA Ester of Pyridoxal)

To a suspension of pyridoxal hydrochloride (1.0 g) in methylene chloride (20 ml) was added triethylamine (2.0 ml). A clear yellow solution developed. With cooling in ice, z,z,z,z,z-eicosa-5,8,11,14,17-pentaenoyl chloride (1.73 g) (prepared by reaction of EPA with oxalyl chloride in methylene chloride). The mixture was stirred overnight under nitrogen, warming up to room temperature. After dilution with an equal volume of methylene chloride, the mixture was extracted with 2M hydrochloric acid (20 ml), washed with water (3×20 ml), dried and concentrated. Purification by flash chromatography (ethyl acetate/hexane) yielded 2-methyl-3-z,z,z,z,z-eicosa-5,8,11,14,17-pentaenoyloxy-4-formyl-5-(z,z,z,z,z-eicosa-5,8,11,14,17-pentaenoyloxy) methyl pyridine as a clear oil.

Example 40

2-Methyl-3-hydroxy-4-formyl-5-(z,z,z-octadeca-6,9,12-trienoyloxy)methyl pyridine (GLA Ester of Pyridoxal)

A solution of z,z,z-octadeca-6,9,12-trienoyl chloride (800 mg, 2.7 mmol) in methylene chloride (10 ml) was added slowly dropwise to a mixture of pyridoxal hydrochloride (500 mg, 2.45 mmol), triethylamine (1 ml, 7.2 mmol) and 4-(N,N-dimethylamino)pyridine (few mg, catalytic amount) in methylene chloride (20 ml) at 0° C. under nitrogen. On completion, as indicated by tlc, the mixture was concentrated and purified by flash chromatography (ethyl acetate/hexane), yielding 2-methyl-3-hydroxy-4-formyl-5-(z,z,z-octadeca-6,9,12-trienoyloxy)methyl pyridine as a colourless oil which subsequently solidified.

Example 41

2-Methyl-3-hydroxy-4,5-di(z,z,z-octadeca-6,9,12-trienoyloxy)methyl Pyridine (Bis GLA Ester of Pyridoxine)

A solution of z,z,z-octadeca-6,9,12-trienoyl chloride (650 mg, 2.2 mmol) in methylene chloride (10 ml) was added slowly dropwise to a mixture of pyridoxine hydrochloride (206 mg, 1 mmol), triethylamine (0.7 ml, 5 mmol) and 4-(N,N-dimethylamino)pyridine (few mg, catalytic amount) in methylene chloride (20 ml) at 0° C.l under nitrogen. On completion, as indicated by tic, (4 h) the mixture was concentrated and purified by flash chromatography (ethyl acetate/hexane), yielding 2-methyl-3-hydroxy-4,5-di(z,z,z-octadeca-6,9,12-trienoyloxy)methyl pyridine as a colourless oil.

Example 42

1-(2-(2-Methyl-5-nitroimidazoloyl)ethyl)-4-(z,z,z-octadeca-6,9,12-trienyl)butane-1,4-dioate (Diester of Metronidazole and GLA Alcohol with Succinic Acid)

A solution of 1,3-dicyclohexylcarbodiimide (780 mg, 3.8 mmol) and 4-(N,N-dimethylamino)pyridine (530 mg, 4.3 mmol) in methylene chloride (15 ml) was added with stirring to a solution of GLA alcohol succinate monoester (1.25 g, 3.3 mmol) (prepared as in Example 27, part 1) and metronidazole (620 mg, 3.6 mmol) in methylene chloride (30 ml) at room temperature under nitrogen. On completion of reaction, as indicated by tlc, the mixture was diluted with hexane, filtered, concentrated and purified by flash chromatography (ethyl acetate/hexane). The product fractions were pooled and concentrated, yielding 1-(2-(2-methyl-5-nitroimidazoloyl)ethyl)-4-(z,z,z-octadeca-6,9,12-trienyl)-1,4-butanedioate as a colourless oil.

Example 43 trans-1-(z,z,z-Octadeca-6,9,12-trienyloxycarbonylbutyloxyamino)-2-phenyl Cyclopropane (Succinic Acid, 1-GLA Alcohol Ester, 4-Tranylcypromine Amide)

A solution of 1,3-dicyclohexylcarbodiimide (315 mg, 1.52 mmol) and 4-(N,N-dimethylamino)pyridine (210 mg, 1.72 mmol) in methylene chloride (10 ml) was added with stirring to a solution of GLA alcohol succinate monoester (500 mg, 1.32 mmol) (prepared as in Example 27, part 1) and tranylcypromine (225 mg, 1.32 mmol) in methylene chloride (20 ml) at room temperature under nitrogen. On completion of reaction, as indicated by tlc, the mixture was diluted with hexane, filtered, concentrated and purified by flash chromatography (ethyl acetate/hexane). The product fractions were pooled and concentrated, yielding trans-1-(z,z,z-octadeca-6,9,12-trienyloxycarbonyl butyloxyamino)-2-phenyl cyclopropane as a colourless oil.

Example 44

(±)-2,5,7,8-tetramethyl-2-(4',8',12'-trimethyldecyl)-6-chromanyl-z,z,z-octadeca-6,9,12-trienoate (GLA ester of α-Tocopherol).

z,z,z-Octadeca-6,9,12-trienoyl chloride (2.96 g, 10 mmol) was added dropwise with stirring over the course of 2–3 minutes to a solution of (±)-α-tocopherol (4.3 g, 10 mmol) and pyridine (0.885 ml, 11 mmol) in methylene chloride (35 ml) under nitrogen at −5° C. The reaction was then stirred overnight, warming up to room temperature. Tlc analysis showed that the reaction had gone substantially towards completion. The reaction mixture was washed with water (100 ml), 2M hydrochloric acid (10 ml in 100 ml water) and water (4×100 ml). The organic layer was dried (sodium sulfate) and concentrated. Purification by flash chromatography (ether/hexane) yielded (±)-2,5,7,8-tetramethyl-2-(4',8',12'-trimethyldecyl)-6-chromanyl-z,z,z-octadeca-6,9,12-trienoate as a pale yellow oil.

Example 45

Androst-5-en-17-one-3-(z,z,z,z,z,z-docosa-4,7,10,13,16,19-hexaenoate)

(DH Ester of Dehydroepiandrosterone)

To a cooled (0° C) mixture of dehydroepiandrosterone (1 g) and triethylamine (1 ml) in methylene chloride (20 ml) was added z,z,z,z,z,z-docosa-4,7,10,13,16,19-hexaenoyl chloride (1.33 g) (prepared by reaction of DHA with oxalyl chloride in methylene chloride). The mixture was stirred overnight, warming up to room temperature. It was diluted with methylene chloride (20 ml), extracted with 2M hydrochloric acid (20 ml), washed with water (2×20 ml), dried and concentrated. Purification by flash chromatography (ethyl acetate/hexane) yielded dehydroepiandrost-5-en-17-one-3 (z,z,z,z,z,z-docosa-4,7,10,13,16,19-hexaenoate) as a clear oil.

Example 46 z,z,z-Octadeca-6,9,12-trienyl-(2-(z,z,z-octadeca-6,9,12-trienyloxy)acetate)

Diester of GLA and GLA Alcohol with Glycolic Acid.

Part 1:

A solution of chloroacetyl chloride (0.4 ml, 5 mmol) in methylene chloride (10 ml) was added dropwise to a solution of z,z,z-octadeca-6,9,12-trienol (1 g, 3.8 mmol) and triethylamine (1.4 ml, 10 mmol) in methylene chloride (20 ml) at 0° C. Progress of reaction was monitored by tlc. After 3 h the reaction had gone substantially but not completely towards completion. A few more drops of chloroacetyl chloride were added. Tlc analysis within 5 minutes showed the reaction to be complete. The mixture was washed with water (2×50 ml) and brine (50 ml), dried (sodium sulfate) and concentrated. Toluene (50 ml) was added to remove azeotropically last traces of water. This yielded the chloroacetyl ester of GLA alcohol as a dark brown oil which was used without further purification.

Part 2:

A mixture of z,z,z-octadeca-6,9,12-trienoic acid (700 mg, 2.5 mmol) and cesium carbonate (410 mg, 1.25 mmol) was swirled in methanol until a clear solution resulted. The mixture was then concentrated and kept at 40° C. under high vacuum for 1 h. This yielded the cesium salt of GLA which was used without further purification.

Part 3:

To the flask containing the cesium salt of GLA as prepared in part 2, was added the chloroacetyl ester of GLA alcohol (part 1) (500 mg, 1.5 mmol) and dry DMF (15 ml). The reaction was stirred under nitrogen at room temperature. After 90 minutes, tlc analysis showed the reaction to be complete. The reaction mixture was extracted with hexane (2×40 ml) and the hexane extract washed with brine (2×50 ml) and water (50 ml), dried (sodium sulfate) and concentrated to yield z,z,z-octadeca-6,9,12-trienyl-(2-(z,z,z-octadeca-6,9,12-trienyloxy)acetate) as a colourless oil.

Example 47

Hydrocortisone-21-(z,z,z-octadeca-6,9,12-trienoate)

(GLA Ester of Hydrocortisone)

A solution of z,z,z-octadeca-6,9,12-trienoyl chloride (450 mg, 1.52 mmol) in methylene chloride (10 ml) was added slowly dropwise to a mixture of hydrocortisone (500 mg, 1.38 mmol), triethylamine (420 μl, 3 mmol) and 4-(N,N-dimethyl amino)pyridine (few mg, catalytic amount) in methylene chloride (20 ml) at 0° C. under nitrogen. Tlc analysis after 4 h indicated that the reaction had gone to completion. The mixture was concentrated and purified by flash chromatography (ethyl acetate/hexane), yielding hydrocortisone-21-(z,z,z-octadeca-6,9,12-trienoate) as a colourless oil.

Example 48 z,z,z-Octadeca-6,9,12-trienyl-(2-(1-(4-chlorobenzoyl)-5-methoxy-2-methylindole-3-acetyloxy)acetate)

Diester of Indomethacin and GLA Alcohol with Glycolic Acid.

Part 1:

A mixture of indomethacin (895 mg, 2.5 mmol) and cesium carbonate (410 mg, 1.25 mmol) was swirled in methanol until a clear solution resulted. The solution was then concentrated and kept at 40° C. under high vacuum for 1 h. This yielded the cesium salt of indomethacin as a bright yellow solid.

Part 2:

To the flask containing the cesium salt of indomethacin as prepared in part 1 was added the chloroacetyl ester of GLA alcohol (prepared as in Example 46 (part 1) (500 mg, 1.5 mmol) and dry DMF (15 ml). The reaction was stirred under nitrogen at room temperature, progress of reaction being monitored by tlc. After an overnight period in the fridge, tlc analysis showed the reaction to be complete. The mixture was partitioned between water (50 ml) and ethyl acetate (50 ml). A few ml of brine were added to break the emulsion. The ethyl acetate layer was washed with water (3=ml), dried (sodium sulfate), filtered through a pad of silica and concentrated to yield z,z,z-octadeca-6,9,12-trienyl-(2-(1-(4-chlorobenzoyl)-5-methoxy-2-methylindole-3-acetyloxy) acetate) as a bright yellow oil.

Example 49

1-(z,z,z-Octadeca-6,9,12-trienoyloxy)-3-(4-phenylbutanoyloxy)propane

Diester of 4-Phenylbutanoic Acid and GLA with 1,3-propane Diol).

A solution of 1,3-dicyclohexylcarbodiimide (710 mg, 3.45 mmol) and 4-(N,N-dimethylamino)pyridine (475 mg, 3.9 mmol) in methylene chloride (10 ml) was added to a solution of 1-(z,z,z-octadeca-6,9,12-trienoyloxy)-3-hydroxypropane (1 g, 3 mmol) and 4-phenylbutanoic acid (520 mg, 3.15 mmol) in methylene chloride (15 ml). The resultant mixture was stirred at room temperature under nitrogen until it was complete as indicated by tlc. The mixture was filtered, concentrated and purified by flash chromatography to yield 1-(z,z,z-octadeca-6,9,12-trienoyloxy)-3-(4-phenylbutanoyloxy)propane.

Example 50

1-(z,z,z-Octadeca-6,9,12-trienoyloxy)-3-(phenylacetoxy)propane (Diester of Phenylacetic Acid and GLA with 1,3-Propane Diol)

In a similar manner to Example 49 but replacing the 4-phenylbutanoic acid with phenylacetic acid (430 mg, 3.15 mmol) was prepared 1-(z,z,z-octadeca-6,9,12-trienoyloxy)-3-(phenylacetoxy)propane.

Example 51

1-(z,z,z-Octadeca-6,9,12-trienoyloxy)-3-(trans-cinnamoyloxy)propane (Diester of trans-Cinnamic Acid and GLA with 1,3-Propane Diol)

In a similar manner to Example 49 but replacing the 4-phenylbutanoic acid with trans-cinnamic acid (470 mg, 3.15 mmol) was prepared 1-(z,z,z-octadeca-6,9,12-trienoyloxy)-3-(trans-cinnamoyloxy)propane.

What is claimed is:

[1. A compound having the formula:

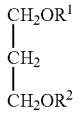

wherein $R^1$ is selected from the group consisting of fatty acid acyl groups of 12 to 30 carbon atoms and fatty alcohol groups of 12 to 30 carbon atoms, and wherein $R^2$ is selected from the group consisting of fatty acid acyl groups of 12 to 30 carbon atoms and fatty alcohol groups of 12 to 30 carbon atoms, the same as or different from $R^1$, the fatty acid acyl or alcohol groups $R^2$ being selected from the group consisting of γ-linoleic acid (GLA), dihomo-γ-linolenic acid (DGLA), arachidonic acid (AA), adrenic acid, stearidonic acid (SA), eicosapentaenoic acid (EPA), docosapentaenoic acid n-3, docosahexaenoic acid (DHA), columbinic acid (CA), parinaric acid and conjugated linoleic acid (cLA) groups.]

[2. The compound according to claim 1, wherein each said fatty acid or fatty alcohol group has 16 to 30 carbon atoms.]

[3. The compound according to claim 1, having a phosphate, succinate, or other difunctional-acid linking moiety between $R^1$ and the corresponding diol oxygen, between $R^2$ and the corresponding diol oxygen, or both.]

[4. The compound according to claim 1, wherein one of $R^1$ and $R^2$ is an acyl moiety corresponding to an acid selected from the group consisting of γ-linolenic acid (GLA) and dihomo-γ-linolenic acid (DGLA), and the other of $R^1$ and $R^2$ is an acyl moiety corresponding to an acid selected from the group consisting of γ-linolenic acid (GLA), dihomo-γ-linolenic acid (DGLA), stearidonic acid (SA), eicosapentaenoic acid (EPA), docosahexaenoic acid (DHA), conjugated linoleic acid (cLA), and columbinic acid (CA).]

[5. The compound according to claim 1, wherein one of $R^1$ and $R^2$ is an acyl moiety corresponding to an acid selected from the group consisting of arachidonic acid (AA), and the other is an acyl moiety corresponding to an acid selected from the group consisting of arachidonic acid (AA), γ-linolenic acid (GLA), dihomo-γ-linolenic acid (DGLA), docosahexaenoic acid (DHA), and eicosapentaenoic acid (EPA).]

[6. The compound according to claim 1, wherein one of the $R^1$ and $R^2$ is an acyl moiety corresponding to eicosapentaenoic acid (EPA) and the other is an acyl moiety corresponding to an acid selected from the group consisting of eicosapentaenoic acid (EPA) and docosahexaenoic acid (DHA).]

[7. A pharmaceutical composition comprising an effective amount of the compound of claim 1 and a suitable diluent or carrier.]

[8. A compound according to claim 1 having the following 1,3-propane diol linked structure:

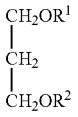

wherein $R^1$ and $R^2$ are pairs of fatty acids selected from the group of pairs of fatty acids consisting of:

γ-linolenic acid and oleic acid; γ-linolenic acid and γ-linolenic acid; eicosapentaenoic acid and eicosapentaenoic acid; γ-linolenic acid and eicosapentaenoic acid; γ-linolenic acid and docosahexaenoic acid; arachidonic acid and docosahexaenoic acid; arachidonic acid and eicosapentaenoic acid; γ-linolenic acid and arachidonic acid; γ-linolenic acid and stearidonic acid; stearidonic acid and docosahexaenoic acid; arachidonic acid and stearidonic acid; dihomo-γ-linolenic acid and dihomo-γ-linolenic acid; dihomo-γ-linolenic acid and γ-linolenic acid; dihomo-γ-linolenic acid and stearidonic acid; dihomo-γ-linolenic acid and arachidonic acid; dihomo-γ-linolenic acid and eicosapentaenoic acid; dihomo-γ-linolenic acid and docosahexaenoic acid; arachidonic acid and arachidonic acid; eicosapentaenoic acid and stearidonic acid; eicosapentaenoic acid and docosahexaenoic acid; docosahexaenoic acid and docosahexaenoic acid; conjugated linoleic acid and conjugated inoleic acid, conjugated linoleic acid and γ-linolenic acid; conjugated linoleic acid and dihomo-γ-linolenic acid; conjugated linoleic acid and arachidonic acid; conjugated hinoleic acid and stearidonic acid; conjugated linoleic acid and eicosapentaenoic acid; conjugated linoleic acid and docosahexaenoic acid; columbinic acid and columbinic acid; columbinic acid and γ-linolenic acid; columbinic acid and dihomo-γ-linolenic acid; columbinic acid and arachidonic acid; columbinic acid and stearidonic acid; columbinic acid and eicosapentaenoic acid; and columbinic acid and docosahexaenoic acid.]

[9. The compound according to claim 8, wherein $R^1$ and $R^2$ are both docosahexaenoic acid moieties.]

[10. The compound according to claim 8, wherein $R^1$ and $R^2$ are both eicosapentaenoic acid moieties.]

[11. A pharmaceutical composition comprising an effective amount of the compound of 8, 9 or 10 and a suitable diluent or carrier.]

*12. A compound having the formula:*

$$R^1OCH_2—CH_2—CH_2OR^2$$

*wherein $R^1$ is selected from the group consisting of fatty acid acyl groups of 12 to 30 carbon atoms and fatty alcohol groups of 12 to 30 carbon atoms, and wherein $R^2$ is lipoic acid.*

*13. A compound having the formula:*

$$R^1OCH_2—CH_2—CH_2OR^2$$

*wherein $R^1$ is selected from the group consisting of fatty acid acyl groups of 12 to 30 carbon atoms and fatty alcohol groups of 12 to 30 carbon atoms, and wherein $R^2$ is a tryptophan, phenylalanine, GABA, fluoextine, or tranylcypromine moiety.*

*14. The compound according to claim 13, wherein $R^1$ is is γ-linolenic acid (GLA) and $R^2$ is tryptophan.*

*15. The compound according to claim 13, wherein $R^1$ is is γ-linolenic acid (GLA) and $R^2$ is phenylalanine.*

*16. The compound according to claim 13, wherein $R^1$ is is γ-linolenic acid (GLA) and $R^2$ is GABA.*

*17. The compound according to claim 15, wherein $R^1$ is is γ-linolenic acid (GLA) and $R^2$ is phenylalanine.*

*18. The compound according to claim 15, wherein $R^1$ is is γ-linolenic acid (GLA) and $R^2$ is GABA.*

* * * * *